United States Patent
Gabriel

(10) Patent No.: US 10,252,254 B2
(45) Date of Patent: Apr. 9, 2019

(54) REMOVABLE PROTECTIVE COATING FOR THE RECEIPT OF A DUST FREE CATALYST

(71) Applicant: CLARIANT INTERNATIONAL LTD., Muttenz (CH)

(72) Inventor: Wolfgang Gabriel, Rosenheim (DE)

(73) Assignee: CLARIANT INTERNATIONAL LTD. (CH)

( * ) Notice: Subject to any disclaimer, the term of this patent is extended or adjusted under 35 U.S.C. 154(b) by 258 days.

(21) Appl. No.: 14/777,390

(22) PCT Filed: Mar. 19, 2014

(86) PCT No.: PCT/EP2014/055529
§ 371 (c)(1),
(2) Date: Sep. 15, 2015

(87) PCT Pub. No.: WO2014/147137
PCT Pub. Date: Sep. 25, 2014

(65) Prior Publication Data
US 2016/0030937 A1    Feb. 4, 2016

(30) Foreign Application Priority Data
Mar. 22, 2013 (EP) ................... 13160611

(51) Int. Cl.
B01J 27/198    (2006.01)
B01J 35/00    (2006.01)
(Continued)

(52) U.S. Cl.
CPC ............. B01J 33/00 (2013.01); B01J 27/198 (2013.01); B01J 35/023 (2013.01); B01J 35/026 (2013.01);
(Continued)

(58) Field of Classification Search
None
See application file for complete search history.

(56) References Cited

U.S. PATENT DOCUMENTS 2,877,196 A * 3/1959 Reding ................ C09D 191/00
524/488
3,048,553 A * 8/1962 Moss ...................... C08J 3/201
523/306
(Continued)

FOREIGN PATENT DOCUMENTS

CN    1304336    7/2001
CN    101301631 A * 11/2008
(Continued)

OTHER PUBLICATIONS

Machine Translation of JP 04358542 A, Dec. 1992 (Year: 1992).*
(Continued)

*Primary Examiner* — Jeffrey A Vonch

(57) ABSTRACT

The invention pertains to a stabilized catalyst mold comprising a catalyst body formed of a catalyst material, said catalyst material comprising a catalytically active material or a precursor material of the catalytically active material, characterized in that at least parts of the surface of the catalyst mold are provided with a protective coating comprising an organic binder. Further, the invention pertains to a method for obtaining a stabilized catalyst mold.

5 Claims, 9 Drawing Sheets

(51) Int. Cl.
*B01J 33/00* (2006.01)
*B01J 37/02* (2006.01)
*B01J 35/02* (2006.01)
*C09D 123/08* (2006.01)
*C09D 131/04* (2006.01)
*C07C 51/215* (2006.01)
*C07C 57/145* (2006.01)
*B01J 23/22* (2006.01)
*B01J 37/00* (2006.01)

(52) U.S. Cl.
CPC .... *B01J 37/0219* (2013.01); *C09D 123/0853* (2013.01); *C09D 131/04* (2013.01); *B01J 23/22* (2013.01); *B01J 37/0009* (2013.01); *B01J 2219/302* (2013.01); *B01J 2219/30223* (2013.01); *B01J 2219/30475* (2013.01); *B01J 2523/51* (2013.01); *B01J 2523/55* (2013.01); *C07C 51/215* (2013.01); *C07C 57/145* (2013.01)

(56) References Cited

U.S. PATENT DOCUMENTS

| | | | |
|---|---|---|---|
| 3,055,842 A * | 9/1962 | Robinson | B01J 23/22 502/353 |
| 3,107,223 A * | 10/1963 | Wainwright | B01J 23/22 502/159 |
| 3,207,716 A * | 9/1965 | Lippoldt | C09D 5/20 524/310 |
| 3,340,057 A * | 9/1967 | Rosenbaum | G03G 5/0535 430/87 |
| 3,492,258 A * | 1/1970 | Kremer | C09D 123/08 427/154 |
| 4,283,307 A * | 8/1981 | Barone | B01J 23/002 502/202 |
| 4,510,263 A * | 4/1985 | Pereira | C10G 45/08 502/314 |
| 4,569,925 A * | 2/1986 | Yang | B01J 23/002 502/209 |
| 4,677,084 A | 6/1987 | Bergna | |
| 4,699,985 A * | 10/1987 | Bither, Jr. | B01J 27/198 549/259 |
| 4,769,477 A | 9/1988 | Bergna | |
| 4,849,539 A | 7/1989 | Bergna | |
| 4,956,322 A * | 9/1990 | Gouzard | B01J 33/00 502/62 |
| 5,039,649 A * | 8/1991 | Lippert | B01J 25/00 502/301 |
| 5,137,860 A * | 8/1992 | Ebner | B01J 27/198 502/209 |
| 5,168,090 A * | 12/1992 | Ebner | B01J 19/30 502/209 |
| 5,275,996 A * | 1/1994 | Andrews | B01J 23/002 502/209 |
| 5,364,824 A * | 11/1994 | Andrews | B01J 23/002 502/209 |
| 5,491,258 A * | 2/1996 | Watanabe | B01J 23/002 427/154 |
| 5,792,719 A * | 8/1998 | Eberle | B01J 23/002 502/178 |
| 6,048,987 A * | 4/2000 | Groke | B01J 27/198 549/259 |
| 6,294,498 B1 * | 9/2001 | Darcissac | B01J 23/882 502/159 |
| 6,407,030 B1 * | 6/2002 | Groke | B01J 27/198 502/209 |
| 6,528,683 B1 * | 3/2003 | Heidemann | B01J 23/22 428/522 |
| 6,812,351 B2 | 11/2004 | Weiguny et al. | |
| 7,338,918 B2 | 3/2008 | Neto et al. | |
| 7,468,341 B2 | 12/2008 | Conca et al. | |
| 7,491,860 B2 | 2/2009 | Fridman et al. | |
| 7,572,752 B2 | 8/2009 | Conca et al. | |
| 7,592,294 B2 | 9/2009 | Storck et al. | |
| 7,718,158 B2 | 5/2010 | Le-Khac et al. | |
| 8,048,820 B2 | 11/2011 | Brandstädter et al. | |
| 9,254,482 B2 | 2/2016 | Hagemeyer et al. | |
| 9,365,433 B2 | 6/2016 | Hagemeyer et al. | |
| 2001/0029235 A1 * | 10/2001 | Walsdorff | B01J 19/30 502/346 |
| 2003/0036475 A1 * | 2/2003 | Kourtakis | B01J 23/002 502/208 |
| 2003/0114688 A1 * | 6/2003 | Weiguny | B01J 23/002 549/259 |
| 2004/0014990 A1 * | 1/2004 | Storck | B01J 27/198 549/259 |
| 2004/0157731 A1 * | 8/2004 | Wolfe | B01J 33/00 502/159 |
| 2006/0189479 A1 * | 8/2006 | Even | B01J 33/00 502/159 |
| 2006/0241309 A1 * | 10/2006 | Duda | C07C 51/215 549/259 |
| 2007/0032377 A1 * | 2/2007 | Hibst | B01J 23/002 502/202 |
| 2007/0041795 A1 | 2/2007 | Neto et al. | |
| 2007/0270514 A1 * | 11/2007 | Lok | B01J 21/04 518/715 |
| 2008/0177105 A1 * | 7/2008 | Raichle | B01J 23/002 562/534 |
| 2009/0306410 A1 * | 12/2009 | Brandstadter | B01J 19/30 549/262 |
| 2010/0016640 A1 * | 1/2010 | Guckel | B01J 19/30 568/487 |
| 2010/0016644 A1 * | 1/2010 | Forkner | B01J 23/002 568/956 |
| 2011/0105790 A1 * | 5/2011 | Hagemeyer | B01J 23/002 562/598 |
| 2011/0201830 A1 * | 8/2011 | Shan | B01J 27/198 549/257 |
| 2011/0257413 A1 * | 10/2011 | Dobner | B01J 27/198 549/256 |
| 2012/0088652 A1 * | 4/2012 | Brodziak | B01J 33/00 502/150 |
| 2012/0160368 A1 * | 6/2012 | McKenna | B01J 8/002 141/11 |
| 2013/0102455 A1 * | 4/2013 | Haddad | B01J 27/198 502/8 |
| 2014/0336287 A1 * | 11/2014 | Terorde | B01J 23/78 518/717 |

FOREIGN PATENT DOCUMENTS

| Country | Number | Date | Class |
|---|---|---|---|
| EP | 2000206 A1 * | 12/2008 | B01J 33/00 |
| EP | 2000207 A1 * | 12/2008 | B01J 33/00 |
| JP | 54037089 A * | 3/1979 | |
| JP | 55073347 A * | 6/1980 | C07C 51/252 |
| JP | H 01-231941 | 9/1989 | |
| JP | 04358542 A * | 12/1992 | |
| JP | 05049938 A * | 3/1993 | |
| JP | H 05-49938 | 3/1993 | |
| JP | 08024665 A * | 1/1996 | |
| JP | H 11-70333 | 3/1999 | |
| JP | H 11-104499 | 4/1999 | |
| JP | 2002-166180 | 6/2002 | |
| JP | 2002166180 A * | 6/2002 | |
| JP | 2002-233767 | 8/2002 | |
| JP | 2002233767 A * | 8/2002 | |
| JP | 2007-506540 | 3/2007 | |
| JP | 2007111581 A * | 5/2007 | |
| JP | 2007-530252 | 11/2007 | |
| JP | 2007-533424 | 11/2007 | |
| JP | 2008-037693 | 2/2008 | |
| JP | 2008037693 A * | 2/2008 | |
| JP | 2009-511414 | 3/2009 | |
| JP | 2012005992 A * | 1/2012 | |
| KR | 10-2008-0055862 | 6/2008 | |
| WO | WO 92/05870 | 4/1992 | |
| WO | WO-9205870 A1 * | 4/1992 | C07C 51/252 |
| WO | WO-0029108 A1 * | 5/2000 | B01J 37/0219 |

(56) References Cited

FOREIGN PATENT DOCUMENTS

| WO | WO 2009/121626 | 10/2009 | | |
|----|----|----|----|----|
| WO | WO-2012068164 A2 * | 5/2012 | ............ | B01J 23/745 |
| WO | WO 2013/021020 | 2/2013 | | |

OTHER PUBLICATIONS

Machine Translation of JP 2012005992 A, Jan. 2012 (Year: 2012).*
Machine Translation of CN 101301631 A, Jan. 2008 (Year: 2008).*
Machine Translation of JP 2002166180 A, Jun. 2002 (Year: 2002).*
PCT international Search Report for PCT/EP2014/055529, dated May 13, 2014.
PCT Written Opinion of the International Search Authority for PCT/EP2014/055529, dated May 13, 2014.
English Abstract for JP2002-233767, Aug. 20, 2002.
English Abstract for JP2002-166180, Jun. 11, 2002.
English Abstract for JPH05-49938, Mar. 2, 1993.
English Abstract for JP2008-037693, Feb. 21, 2008.
Bibliographic data page from ESPACENET for JPS62144752, published Jun. 27, 1987.
English Translation of State Intellectual Property Office of the People's Republic of China, Notification of the Second Office Action for Chinese Application No. 201480009080.6, dated Mar. 8, 2017.
English English Translation of Office Action for Japanese Patent Application No. 2016-503652, dated Sep. 14, 2016.
English Translation of Office Action for Japanese Patent Application No. 2016-503652, dated Jul. 18, 2017.
English Translation of Office Action for Korean Patent Application No. 10-2015-7026209, dated May 26, 2017.

* cited by examiner

REMOVABLE PROTECTIVE COATING FOR THE RECEIPT OF A DUST FREE CATALYST

The present invention relates to a stabilized catalyst mould comprising a catalyst body, said catalyst body comprising a catalyst material and to a method for producing a stabilized catalyst mould.

Due to their physical properties, many catalysts, as they are used in the chemical industry, cause tremendous dust formation by abrasion and attrition during catalyst handling. Since these catalysts very often comprise harmful or even toxic elements or compounds (e.g. Cr(VI), $V_2O_5$, vanadyl pyrophosphate, noble metals, etc.), the exposition of personnel handling such catalysts to the formed catalyst dust is critical. This aspect especially has to be considered in view of the EU Regulation for Chemicals, called REACH, which will become effective in 2013.

Maleic anhydride is a chemical intermediate of relevant commercial interest. For example, maleic anhydride is used in the production of alkyd and polyester resins, solely or in combination with other acids. Additionally thereto, it represents also an intermediate versatilely usable for chemical synthesis, for example, for the synthesis of γ-butyrolactone, tetrahydrofurane, and 1,4-butanediol, which again are used as solvents or are further processed into polymers, such as poly tetrahydrofurane, or polyvinyl pyrrolidone.

The production of maleic anhydride (MA) is carried out regularly by partial oxidation of hydrocarbons, in particular butane or benzene, in the gas phase with molecular oxygen or with a gas containing molecular oxygen in the presence of a vanadium phosphorus oxide catalyst (VPO catalyst). Different oxidation catalysts, different shapes of catalyst moulds and different procedure conditions are used. Generally, the oxidation catalysts contain mixed oxides of vanadium and phosphorus, wherein such oxidation catalysts containing vanadium with a valence from 3.8 to 4.8 are proven to be especially suitable for the production of maleic anhydride from hydrocarbons having at least four carbon atoms in a straight chain. Additionally to vanadium, phosphorus and oxygen, for example, the VPO catalysts may comprise metals, which may be present in the oxidation catalyst in form of their oxides. By way of example, for the production of maleic anhydride by heterogeneous catalytic gas phase oxidation of hydrocarbons, catalyst moulds are used, which contain vanadium, phosphorus and oxygen and have varying geometry.

For instance, a typical catalyst that is used for the production of maleic anhydride according to the state of the art takes the form of rings or hollow cylinders. These rings or hollow cylinders are made by compressing a powder comprising a catalytically active material or a precursor material of the catalytically active material. Such catalyst moulds show relatively low crush strength, and, therefore, have a strong tendency for abrasion and attrition. If the catalyst rings are stressed mechanically, for example, during the filling of drums after production, during transportation, during drum emptying and finally during reactor loading, heavy dust formation occurs because of abrasion and attrition. A separation of these fines by sieving is only a temporary measure, because any further mechanical stress causes new dust formation.

This significant dust formation leads to serious disadvantages for catalyst handling and use of the catalyst in the reactor.

1. The active component of the catalyst for the production of maleic anhydride comprises vanadyl pyrophosphate, which is considered to be toxic and harmful to the environment. Persons handling this catalyst, e.g. during filling of drums, discharging of drums and reactor loading, have to wear extensive personal protection equipment. Also at every time during catalyst handling, appropriate vacuum systems should be installed, in order to keep the exposition of personnel and environment to the catalyst dust as low as possible. These extensive protection measures are cost intensive and sometimes hard to realize.

2. If catalyst fines end up in the reactor tubes during catalyst loading, unequal pressure drop of the individual reactor tubes might result. However, for a good catalyst performance and safe operation of the reactor, it is important that the pressure drop of individual reactor tubes is kept within a given tolerance. If the pressure drop in individual tubes is out of tolerance due to a significant amount of fines, these tubes must be emptied and have to be refilled, for example, with sieved or fresh catalyst moulds. Besides increased time and work effort also increased costs by the use of additional fresh catalyst moulds will result.

3. Due to the REACH directive of the European Union for the Registration, Evaluation, Authorisation and Restriction of Chemicals, scenarios of the exposition for the complete processing chain must be established. Also under this aspect it would be useful to be able to provide a non-dusting catalyst.

The problem of dust formation during catalyst production and handling is not specifically directed to a distinct catalyst, for example, a catalyst for the production of maleic anhydride or formaldehyde, but is common to all catalysts with low attrition strength.

A further example for a catalyst with low attrition strength is a catalyst for non-oxidative dehydrogenation of hydrocarbons, such as propane, to olefins, such as propylene, by following the Houdry-Catofin®-Process. Such process is e.g. described in US 2007/32691 A1. The catalyst commonly is provided in the form of extrusions with a nominal diameter of e.g. 3 mm. The catalyst comprises $Cr_2O_3$ and alumina. Although chromium is basically comprised as Cr(III), there are always significant amounts of highly toxic Cr(VI) present.

A further example for a catalyst of low attrition resistance is an iron molybdate catalyst for the production of formaldehyde from methanol, as it is disclosed e.g. in US 2006/0 142 619 A1. This catalyst comprises a mixture of $Fe_2(MoO_4)_3$ and $MoO_3$, in which the Mo/Fe atomic number ratio is from 1.5 to 5.

US 2006/0 135 821 A1 discloses a catalyst for oxidation of methanol to formaldehyde similar to the above. The method to prepare the catalyst comprises mixing of raw materials in aqueous solution, which solution is then fed to a spray dryer. The resulting powder is converted, after lubrication, into cylindrical pellets with a three-lobed cross section. Through bores are provided at the lobes. Calcination of the pellets at 500° C. for four hours leads to the formation of the catalyst.

During filling a reactor with catalyst material, in particular with catalyst bodies formed of 100% active material, it is almost impossible to completely safeguard the workers against pollution by dust. The filling of a typical reactor as used for production in industrial scale lasts for about four to six days, wherein up to 30 tons of catalyst material is filled into the reactor.

The problem underlying the invention therefore is to provide a measure that allows minimization of dust formation during catalyst production and handling, to thereby e.g. reduce exposition of personnel working with this catalyst.

This problem is solved by a stabilized catalyst mould according to claim 1 and a method for producing a stabilized catalyst mould as defined in independent claim 12. Preferred embodiments are subject of the dependent claims.

According to the invention, the catalyst mould is provided at its outside surface with a protective coating comprising an organic binder that has penetrated into the surface of a catalyst body made of catalyst material. The organic binder penetrates into the catalyst body only for a particular distance from the surface and thereby forms a protective layer together with the catalyst material present at the surface of the catalyst body to thereby stabilize the outer surface of the catalyst mould.

By the protective layer formed at the outer surface of the catalyst mould, the attrition and abrasion resistance of the catalyst mould is increased significantly and almost no dust formation is observed during usual handling of the catalyst moulds according to the invention. Furthermore also edges of the catalyst mould are stabilized and, therefore, the amount of catalyst material breaking off during catalyst handling, e.g. during filling of a reactor, is minimized. The adhesive properties of the protective coating also stabilize cracks that can occur during pelletizing (capping) thereby further minimizing dust formation. Furthermore, due to the outer protective layer formed of binder which provides a smooth surface, the catalyst moulds can slide along each other very smoothly, which further facilitates catalyst handling during e.g. filling of drums for transportation or filling of the reactor.

The organic binder is present only within a layer adjacent to the surface of the catalyst mould whereas the inner portions of the catalyst mould do not comprise such organic binder.

Since only a very small amount of binder is necessary to form a protective coating at the outside of the catalyst mould, the organic binder can be removed again easily and residue-free, e.g. after the catalyst moulds have been filled into reactor tubes. Removal of the binder can be performed at mild conditions, e.g. during activation of a precursor material of the catalytically active material comprised in the catalyst material e.g. by heating the catalyst mould, e.g. in an oxygen-containing atmosphere, like air. Since the protective coating formed of the organic binder is easily removable, the essential parameters of the catalytically active material, such as its BET surface area, its pore volume and pore size distribution, remain unchanged during removal of the organic binder or are at least not changed adversely, when compared with parameters of a catalyst prepared without application of a protective coating. The catalyst performance, e.g. the activity of the catalytically active material, and the catalyst lifetime therefore are not influenced adversely by application of the protective coating comprising the organic binder. To the opposite, due to the lower amount of dust produced during reactor filling, the lifetime of the catalyst can be increased and the overall efficiency of a reactor loading can be improved, e.g. by a reduced power consumption of a compressor used for feeding a reaction gas to the reactor.

The amount of binder needed to form the protective coating can be chosen very small and, therefore, catalyst moulds do not adhere to each other when applying the organic binder to the catalyst body but remain in a free-flowing state. Due to a porosity provided by the catalyst material of the catalyst body, the binder, when applied to the catalyst body, is immediately absorbed during application and no sticky film of binder forms on the catalyst mould surface. Formation of twins or larger clumps of catalyst moulds is therefore reliably avoided. Furthermore, due to the low amount of binder comprised in the catalyst moulds according to the invention, the binder can be removed quite easily under mild reaction conditions. Removal of the binder can be performed e.g. during activation of the catalyst without leaving behind any residue that may adversely influence the catalyst activity or performance.

A general embodiment of the present invention therefore is directed to a stabilized catalyst mould comprising a catalyst body formed of a catalyst material, said catalyst material comprising a catalytically active material or a precursor material of the catalytically active material, characterized in that at least parts of the surface of the catalyst body are provided with a protective coating comprising an organic binder.

According to an embodiment, at least the outer geometric surface of the catalyst mould is provided with the protective coating comprising an organic binder. The geometric surface of a catalyst mould or a catalyst body is understood to be the surface of a geometric form that corresponds to the form of the catalyst mould or catalyst body. E.g. when the catalyst mould takes the form of a sphere, the geometric surface is the surface of sphere ($4\pi r^2$). The geometric form does not have porosity but has a smooth and tight surface.

The outer geometric surface is understood to be those parts of the catalyst mould surface that can get into contact with each other during catalyst handling, e.g. when filling a reactor, to rub against each other, thereby causing attrition. Catalyst moulds may comprise e.g. bore holes, e.g. when taking the form of a hollow cylinder. Such protected parts of the catalyst mould geometric surface are understood as inner geometric surfaces of the catalyst mould. An inner geometric surface is e.g. the surface formed by the bore hole of a hollow cylinder.

Preferably at least 50% of the catalyst mould geometric surface is provided with a protective coating comprising an organic binder. According to a further embodiment, at least 70% of the catalyst mould geometric surface is provided with a protective coating comprising an organic binder and according to a still further embodiment at least 90% of the catalyst mould geometric surface is provided with a protective coating comprising an organic binder.

According to a still further embodiment, the complete geometric surface (100%) of the catalyst mould is provided with a protective coating comprising an organic binder.

The term "surface" denotes a geometrical surface of the catalyst mould and can be e.g. the surface of a cylinder or a sphere.

The catalyst mould according to an embodiment has a homogeneous composition in view of the catalyst material, i.e. before application of the organic binder. According to an embodiment, the catalyst mould is not a shell catalyst comprising an inert carrier surrounded by a shell comprising at least one layer of catalyst material comprising catalytically active material or a precursor material thereof.

A catalyst mould is understood to be a catalyst body provided at least in parts of its outer geometric surface with a protective coating comprising an organic binder.

A catalyst body is understood to be a body of a particular shape comprising a catalyst material. The catalyst body does not comprise a protective coating comprising an organic binder.

A protective coating is understood to be a layer formed of organic binder and of catalyst material wherein particles of the catalyst material are joined together by the organic binder such that a layer at the outer surface of the catalyst body is formed to thereby form the protective coating of the catalyst mould in at least parts of its geometric surface.

A catalyst material is understood to be a material comprising a catalytically active material or a precursor material of the catalytically active material.

Besides the catalytically active material or the precursor material of the catalytically active material the catalyst material may comprise further components, e.g. inert solid diluents, pore formers, e.g. sawdust, tabletting aids, lubricants, etc. that preferably are removed during catalyst activation.

A catalytically active material is understood to be a compound or material that is provided in its active form and catalyses a particular reaction, e.g. an oxidation reaction.

A precursor material of the catalytically active material is understood to be a compound or a material that can be transformed into the catalytically active material, preferably by chemical or thermal reaction, e.g. by transforming the precursor material into an oxide.

According to an embodiment the catalyst material comprises at least 50 wt.-% of catalytically active material or its equivalent of precursor material of the catalytically active material. According to a further embodiment the catalyst material comprises at least 70 wt.-% and according to a still further embodiment comprises at least 90 wt.-% of catalytically active material or its equivalent of precursor material of the catalytically active material.

In an embodiment the catalyst material is made up to 100 wt.-% of catalytically active material or its equivalent of precursor material.

According to an embodiment, the catalyst body consists of catalyst material.

According to the invention an organic binder is used for fixation and stabilization of an outer layer of the catalyst mould or catalyst body, thereby forming a protective coating.

Basically any organic material can be used as organic binder that has an adhering effect. Small binder molecules may be suitable for formation of a protective coating, e.g. glycerol. However, better results as to stability of the catalyst moulds are obtained when using an organic binder having a higher molecular weight, e.g. a polymer.

According to an embodiment the organic binder being provided at least in parts of the surface of the catalyst mould and forming a protective coating, has a number average molecular weight of at least 100 g/mol, according to a further embodiment has a number average molecular weight of at least 500 g/mol, according to a further embodiment has a number average molecular weight of at least 1.000 g/mol, according to a further embodiment has a number average molecular weight of at least 2.000 g/mol, according to a further embodiment of at least 5.000 g/mol, and according to a still further embodiment of at least 10.000 g/mol. According to a further embodiment, the organic binder being provided at least in parts of the surface of the catalyst mould for forming a protective coating, has a number average molecular weight of less than 500.000 g/mol, according to a further embodiment of less than 200.000 g/mol.

According to an embodiment, the organic binder comprises or is formed of a polymer. The polymer basically may have any structure and can be e.g. a linear or a branched polymer. The polymer can be crosslinked or can have a structure without cross-links.

According to an embodiment the polymer has a linear structure.

In a further embodiment, the polymer is formed as a copolymer of at least two monomers. According to an embodiment the copolymer is formed of exactly two or exactly three monomers.

As described already for the polymer, the copolymer can have any structure and can have a linear structure or a branched structure or can be cross-linked.

According to a further embodiment, the copolymer of the organic binder is a linear copolymer.

In an embodiment, the polymer, according to an embodiment the copolymer of the organic binder is comprised of atoms, selected from the group consisting of carbon, hydrogen, oxygen and nitrogen, and, according to an embodiment, is selected from the group consisting of carbon, hydrogen, and oxygen. According to an embodiment the copolymer of the organic binder consists of atoms, selected from the group consisting of carbon, hydrogen, oxygen and nitrogen, and, according to a still further embodiment, consists of atoms selected from the group consisting of carbon, hydrogen, and oxygen In an embodiment, the organic binder comprises a copolymer of a first vinyl monomer and at least one further monomer that is polymerizable. The further monomer comprises according to an embodiment at least one, according to an embodiment exactly one carbon-carbon double bond that can be polymerized.

The further monomer can be a further vinyl monomer. The further vinyl monomer is different from the first vinyl monomer. The further vinyl monomer can be a vinyl monomer of a particular structure, i.e. a second vinyl monomer, or can be a mixture of vinyl monomers, i.e. comprise a second, third, etc. vinyl monomer.

According to an embodiment, the first vinyl monomer is selected from the group of vinyl acetate, vinyl alcohol, vinyl pyrrolidone.

The further monomer, according to an embodiment, is selected from the group of vinyl monomers, in particular the vinyl monomers mentioned above for the first vinyl monomer, ethylene, propylene and/or maleic anhydride. The monomers can be used alone or in combination with each other.

According to a further embodiment, a polyvinylacetate, in particular a polyvinylacetate comprising vinyl acetate and ethylene as monomers, is used as the organic binder. Polyvinyl acetate, in particular a polyvinyl acetate comprising vinyl acetate and ethylene monomers, is water-insoluble but can be easily dispersed in water and therefore can be applied to the catalyst body e.g. by spraying an emulsion or suspension of the polymer or copolymer onto the catalyst bodies, which are preferably agitated during spraying or by e.g. impregnating the catalyst body with an emulsion or suspension of the polymer or copolymer.

At elevated temperature, e.g. at temperatures of 300° C. to 500° C., the organic binder, according to an embodiment the polyvinylacetate, in particular the polyvinyl acetate copolymer, decomposes, e.g. to acetic acid, carbon dioxide and water and, therefore, can easily be removed from the catalyst mould, e.g. during activation of the precursor material of the catalytically active material.

According to an embodiment, the copolymer used as an organic binder comprises vinyl alcohol monomers.

Further, according to an embodiment, the copolymer forming the organic binder comprises maleic acid monomers.

In an alternative embodiment, the polymer used as organic binder in the catalyst mould according to the invention comprises only one monomer, according to an embodiment vinyl acetate.

According to an embodiment, the polymer comprised in the organic binder is a partially saponified polyvinyl acetate, so that the chemical nature of this polymer can also be described as "copolymer of poly(vinyl alcohol—vinyl acetate)".

The term "polyvinyl acetate", as it is used in the sense of the present invention, refers to a polymer comprising normal or unhydrolysed vinyl acetate monomers. A polyvinyl acetate, according to an embodiment, can also comprise vinyl alcohol monomers, so that, according to an embodiment, both, free OH-groups and OH-groups esterified with acetic acid are present simultaneously in the polyvinyl acetate.

According to a further embodiment the polymer forming the organic binder is a poly(meth)acrylate, such as acrylic/methacrylate ester, methyl-(meth)acrylate/butyl (meth)acrylate, 2-ethylhexyl(meth)acrylate and other (meth)acrylates. The advantage of poly(meth)acrylate binders is that they decompose at relatively low temperatures without forming organic acids.

A further embodiment of the present invention relates to water-soluble cellulose derivatives as polymer comprised in the organic binder, preferably to cellulose ethers and esters. Amongst cellulose ethers, hydroxyethyl cellulose and hydroxypropyl cellulose is preferred; whereas amongst cellulose esters, cellulose acetate is preferred.

Hydroxyethyl cellulose is non-toxic and decomposes at temperatures above 200° C. under excess oxygen in a residue-free manner into $CO_2$ and water. Hydroxyethyl cellulose is water soluble and, therefore, can be applied to the catalyst body e.g. by spraying or impregnating. During drying a stable film forms that has adhesive properties thereby forming a protective coating in the sense of the present invention on the surface of the catalyst mould.

According to a further embodiment starches, modified starches, dextrines, and dextrines being modified with a plasticizer, e.g. polypropylene, are used as polymers comprised in the organic binder.

As already described above, only low amounts of binder are necessary to stabilize the catalyst mould and to reduce or prevent dust formation.

The amount of organic binder comprised in the catalyst mould according to an embodiment is selected as low as possible, so that catalyst mould is merely penetrated in an exterior layer by the organic binder thereby forming a thin protective coating.

According to an embodiment, the protective coating embraces less than 50% of the volume of the catalyst mould, according to an embodiment embraces less than 20% of the volume of the catalyst mould, according to a further embodiment embraces less than 10%, according to a further embodiment embraces less than 5%, according to a further embodiment embraces less than 2% of the volume of the catalyst mould. According to an embodiment, the protective coating embraces more than 0.01% of the volume of the catalyst mould, according to an embodiment embraces more than 0.1% of the volume of the catalyst mould. As already described above, the volume embraced by the protective coating is located adjacent to the outer surface of the catalyst mould such that, according to an embodiment, the inner parts of the catalyst mould can remain free of organic binder.

The depth of penetration, i.e. the thickness of the protective coating, according to an embodiment is less than 300 μm. The minimum depth of penetration, i.e. the thickness of the protective coating, according to a further embodiment is at least about 50 μm. The organic binder preferably does not form a layer of significant thickness being present on the outside of the catalyst mould, i.e. the organic binder has almost completely penetrated into the catalyst body.

Due to the small amount of the organic binder and the low penetration depth of the organic binder into the catalyst body, contiguous catalyst moulds do not adhere to each other. During application of the organic binder, e.g. in the form of a solution, an emulsion or a suspension, the catalyst bodies have a "dry" appearance and are free-flowing. The exterior layer of the adhesive, i.e. the layer of organic binder that has not penetrated into the catalyst mould, according to an embodiment has a layer thickness of less than 10 μm after drying.

According to an embodiment, the amount of organic binder comprised in the catalyst mould according to the invention is at least 0.05 weight-%, according to a further embodiment is at least 0.1 weight-%, and according to a still further embodiment is at least 0.25 weight-%, each in relation to the weight of the catalyst mould. In another embodiment, the amount of the organic binder comprised in the catalyst mould is at most 5.0 wt. %, according to a further embodiment at most 1.0 weight-%, according to a further embodiment is at most 0.75 weight-%, and according to a still further embodiment is at most 0.5 weight-%, each in relation to the weight of the catalyst mould. The percentages refer to the organic binder without any solvent.

In the catalyst mould according to the invention the binder forms a protective coating together with the catalyst material present near or at the outside surface of the catalyst mould. The catalyst material or the catalyst body is porous such that the binder can penetrate into the material when applied to the catalyst body in liquid form, e.g. in the form of a solution, a suspension or an emulsion.

According to an embodiment, the penetration depth of the organic binder into the catalyst mould, i.e. the thickness of the protective coating, is at most 300 μm, according to a further embodiment at most 200 μm, and according to a still further embodiment is at most 100 μm. To provide sufficient stability to the catalyst mould, according to an embodiment, the penetration depth of the organic binder into the catalyst mould, i.e. the thickness of the protective coating, is at least 50 μm.

In an embodiment, the catalyst mould is free-flowing.

The catalyst mould basically can have any form and any size.

According to an embodiment, the catalyst mould has a maximum extension of 20 mm, according to a further embodiment a maximum extension of 10 mm, according to a further embodiment a maximum extension of 5 mm, according to a further embodiment a maximum extension of 4 mm, and according to a still further embodiment a maximum extension of 3 mm.

According to a further embodiment, the catalyst mould has a maximum extension of at least 1 mm, according to a further embodiment has a maximum extension of at least 2 mm.

The geometry of a catalyst mould generally is independent of both the chemical nature of the catalytically active material and the type of the reaction catalysed by the catalyst. However, in particular cases, a distinct shape of the catalyst mould might be preferred for a distinct catalyst and reaction due to particular reasons, such as yield and selectivity, pressure drop, heat and mass transport phenomena and the like. Therefore, principally all geometric shapes of a catalyst body or mould can be used to perform the present invention.

According to an embodiment, the catalyst mould can take the form of a massive body, e.g. a cylinder, a sphere, a circular tablet etc.

According to a further embodiment, the catalyst mould has at least one bore hole, according to an embodiment exactly one bore hole or exactly two bore holes. The catalyst mould can then take the geometric form of e.g. a ring or a hollow cylinder. The front surfaces of the hollow cylinder according to an embodiment can be chamfered both in direction of the outer edge and the edge of the inner bore hole or in either one direction, e.g. in the direction of the outer edge.

The bore hole according to an embodiment has diameter of at least 1 mm, according to a further embodiment of at least 2 mm. According to a further embodiment, the diameter of the bore hole is less than 4 mm, according to an embodiment is less than 2.5 mm.

According to an embodiment, the catalyst mould has rotational symmetric geometry.

The catalyst mould may also take other geometrical forms, e.g. a trilobal form, a quadrulobal form or a cuboid form, e.g. the form of a cube or a prism.

According to an embodiment the catalyst mould is designed as catalyst for the production of maleic anhydride e.g. by heterogeneously catalysed gas phase oxidation of a hydrocarbon having at least four carbon atoms.

Basically every catalyst material or in other words, every catalytically active material known for the production of maleic anhydride or each precursor material of the catalytically active material can be used for the catalyst material comprised in the catalyst mould according to the invention.

According to an embodiment the catalyst mould comprises a catalyst material comprising vanadium phosphorus mixed oxide or a precursor material of a vanadium phosphorus mixed oxide.

Besides vanadium, phosphorous and oxygen, the catalyst material can comprise further promoters to modify the performance of the catalytically active material.

According to an embodiment, the catalytically active material has a composition according to the general formula $$VP_xO_yM_z$$

wherein M is a promoter, x is a number between 0.1 and 3, y is a number according to the valence of V, P and M and z is a number between 0 and 1.5.

Promoter M can be a metal which is according to a further embodiment be selected from the group formed of chromium, nickel, magnesium, aluminum, silicium, wolfram, niobium, antimony, cesium, and their mixtures.

The catalytically active material can also comprise further promoters. According to a further embodiment, the further promoters are selected from the group of lithium, zinc, iron, bismuth, tellurium, silver, molybdenum, zirconium, and their mixtures.

According to an embodiment, the promoter is present in the form of an oxide or in the form of a precursor compound that can be transformed into an oxide, e.g. by heating in an oxygen-containing atmosphere. According to an embodiment, the promoter or the mixture of promoters is present in amount of 0.005 to 5 wt.-%, calculated as oxide and referring to the total weight of the catalytically active material in its oxidic form.

The BET surface area of the catalyst body, i.e. in a form before application or after removal of the organic binder comprised in the protective layer of the catalyst mould, according to an embodiment is selected within a range of 10 to 300 m²/g, according to a further embodiment is within a range of 12 to 80 m²/g, and according to further embodiment is within a range of 15 to 50 m²/g. The BET surface area is determined using the single-point method by adsorption of nitrogen according to DIN 66132.

According to a further embodiment the integral pore volume (determined according to DIN 66133 (Hg porosimetry)) of the catalyst material, according to an embodiment, of the catalyst body, i.e. in a form before application or after removal of the organic binder comprised in the protective layer of the catalyst mould, is >100 mm³/g, according to a further embodiment is >180 mm³/g. According to a still further embodiment the integral pore volume of the catalyst material or, according to an embodiment, of the catalyst body is <300 mm³/g.

According to a further embodiment the catalyst mould is designed as catalyst for the production of formaldehyde by oxidation of methanol.

According to an embodiment, the catalytically active material comprises iron molybdates. According to a further embodiment, the catalytically active material comprises $Fe_2(MoO_4)_3$ and molybdenum trioxide ($MoO_3$). The Fe/Mo ratio is selected according to an embodiment within a range of higher than 1.5 and lower than 5.

Besides $Fe_2(MoO_4)_3$ and molybdenum trioxide ($MoO_3$) the catalytically active material can comprise further compounds. According to an embodiment the catalytically active material comprises as further compound a compound of cerium, molybdenum and oxygen. According to an embodiment the further compound is present in an amount of 0.1 to 10 wt. %, expressed as cerium.

Suitable catalytically active materials are described e.g. in US 2006/0135821 A1 and US 2006/0142619 A1.

According to a further embodiment the catalyst mould is designed as catalyst for the production of propylene by non-oxidative dehydrogenation of hydrocarbons, such as propane, to olefins, such as propylene. According to this embodiment the catalytically active material comprises Cr (III).

According to a further embodiment, the catalyst mould is designed as a catalyst for the oxidation of hydrocarbons, in particular for the production of acrylic acid by oxidation of propane. According to such embodiment, the catalytic material comprises molybdenum, vanadium, niobium, tellurium, manganese and cobalt, wherein the molar ratio of at least one element, selected from manganese and cobalt, and molybdenum is within a range of 0.01 to 0.2, preferably 0.02 to 0.15, more preferred is within a range of 0.03:1 to 0.1:1. According to an embodiment, the catalytic material is formed of a mixed oxide of the formula:

$$MoV_aNb_bTe_cMn_dCo_eNi_fO_x$$

wherein at least one of the following prerequisites applies:
a=0.22 or 0.23
b=0.18 or 0.195
c=0.18 or 0.196
d=0.07 or 0.08
e=0.0375
f=0 or 0.02, and
x=2.635 or the molar number determined by the valence and the amount of elements different from oxygen.

According to a further embodiment, the catalyst mould is designed as a catalyst for the oxidation of acrolein to obtain acrylic acid. The catalytic material according to this embodiment is a nanocrystalline mixed molybdenum oxide obtained by
a) introducing a solution, suspension or slurry which contains a molybdenum starting compound and at least one further metal-containing starting compound, selected from a tungsten-containing and/or vanadium-containing starting compound, into a reaction chamber by means of a carrier fluid,
b) thermal treatment of the solution, suspension or slurry which contains the molybdenum starting compound and the at least one further metal-containing starting compound in a treatment zone by means of a pulsating flow at a temperature of from 200 to 500° C.,
c) formation of nanocrystalline molybdenum mixed oxide,
d) discharge of the nanocrystalline molybdenum mixed oxide obtained in steps b) and c) from the reactor.

Such nanocrystalline mixed molybdenum oxide is described e.g. in WO 2009/121626

According to a further embodiment, the catalyst mould is designed as a catalyst for manufacturing α,β-unsaturated aldehydes by oxidation of olefins. The catalytic material of the catalyst mould is a composite material that can be obtained by
a) providing a first aqueous solution comprising salts of bismuth and nickel or bismuth and cobalt;
b) providing a second aqueous solution comprising an molybdenum compound and optionally a binder agent;
c) adding the first aqueous solution to the second aqueous solution, thereby obtaining a first suspension;
d) adding a second suspension to the first suspension whereby a third suspension is obtained, wherein the second suspension comprises $SiO_2$ having a pore volume in a range of 0.1 to 10 ml/g and an average particle size in a range of 3 to 20 μm;
e) spray calcination of the third suspension at a temperature within a range of 200 to 600° C. whereby a composite material is obtained comprising a bismuth-molybdenum-nickel mixed oxide or a bismuth-molybdenum-cobalt mixed oxide.

Such catalytic material is described e.g. in WO 2013/021020.

According to a further embodiment the catalyst mould according to the invention is designed for the production of maleic anhydride by heterogeneously catalyzed gas phase oxidation of a hydrocarbon having at least four carbon atoms. A catalyst mould according to this embodiment contains a catalytically active material of vanadium phosphorus mixed oxide, or a precursor material thereof, and possesses essentially a hollow-cylindrical structure. The hollow-cylinder is formed according to an embodiment in that the ratio of the height to the diameter of the through-hole is at most 1.5, and, further, the ratio of the geometric surface to the geometric volume of the mould is at least 2 $mm^{-1}$. The geometry of such a catalyst in described e.g. in US 2003/0114 688A1.

According to a further embodiment the catalyst mould according to the invention is intended for the production of maleic anhydride, wherein the mould comprises a massive geometric form with at least one hollow space in the exterior surface. The catalytically active material is formed of a mixed oxide of vanadium and phosphorus. The catalyst mould or the catalyst body has a geometric volume of 30 to 67 percent of the geometric volume the massive geometric form would have taken without the hollow space, wherein the ratio of the geometric surface of the catalyst mould or catalyst body to the geometric volume of the catalyst mould or catalyst body is at least 20 $cm^{-1}$. The geometry of catalyst mould or catalyst body is described e.g. in WO 92/05 870.

According to a further embodiment the catalyst mould according to the invention is intended for the production of maleic anhydride and the catalytically active material is containing mixed oxides of vanadium and phosphorus as catalyst components. To improve the properties of the catalyst mould, according to an embodiment the catalyst shape encasing the catalyst mould is a prism having a first and a second triangular area, and the catalyst mould is provided with three continuous holes, which extend from the first area of the mould spanning the first triangular area of the prism to the second area of the mould spanning the second triangular area of the prism. The geometry of such a catalyst mould is described e.g. in US 2009/0306 410 A1.

According to a further aspect the invention pertains to a method for producing a stabilized catalyst mould.

In the method according to the invention a catalyst material comprising a catalytically active material or a precursor of the catalytically active material is provided and is formed into a catalyst body. To the catalyst body is then applied at least in parts of its surface with a layer of an organic binder to obtain a protective coating formed of particles of the catalyst material joined by the organic binder to thereby provide the stabilized catalyst mould.

The shaping of the catalyst body is done by methods known to the skilled artisan.

According to a first embodiment, the catalyst material is shaped to a massive catalyst body. A massive catalyst body is understood to be a catalyst body that is formed in its entirety of the catalyst material. Suitable methods for obtaining such massive catalyst body is e.g. by tabletting or extruding a mass or powder comprising the catalytically active material or a precursor of the catalytically active material. Besides the catalytically active material or the precursor of the catalytically active material usual auxiliary compounds can be comprised in the catalyst material, e.g. pore formers or lubricating agents, e.g. graphite.

According to a second embodiment the catalyst body is formed of an inert support core surrounded by a shell formed of at least one layer of the catalyst material comprising the catalytically active material or the precursor material of the catalytically active material. The catalyst body according to the second embodiment takes the form of a shell catalyst body.

The layer of the shell catalyst body comprising the catalyst material does not comprise a binder, in particular does not comprise an organic binder. The shell of the shell catalyst body therefore is fragile and easily falls off during handling of the shell catalyst body resulting in intense dust formation.

To obtain a shell catalyst body according to the second embodiment of the method according to the invention first a pre-stage shell catalyst body is produced.

To obtain the pre-stage shell catalyst body an inert support core is coated with a pre-stage catalyst material such that the inert support core is surrounded by a shell comprising at least one layer of the pre-stage catalyst material.

The pre-stage catalyst material comprises a catalytically active material or a precursor of the catalytically active material and a binder, in particular an organic binder. Organic binders as commonly used for the production of shell catalysts can be used, e.g. the organic binders as described above.

According to an embodiment, the pre-stage shell catalyst body comprises a precursor of the catalytically active material in its shell.

The pre-stage shell catalyst body is then transformed into the shell catalyst body to be used as a catalyst body in the method according to the invention by heating the pre-stage shell catalyst body in an oxidizing atmosphere, preferably in air, to remove the binder and, according to an embodiment, to transform the precursor of the catalytically active material into the catalytically active material.

The shell of the shell catalyst body used in the second embodiment and comprising the catalytically active material does no longer comprise an organic binder and, therefore, is very fragile and, therefore, easily falls off from the inert support body when experiencing mechanical stress.

By applying a binder, in particular an organic binder, to the fragile shell of the shell catalyst body a catalyst mould is obtained with high mechanical stability that can, e.g., be loaded into the tubes of a reactor without a reasonable amount of the shell falling off from the inert support core.

According to an embodiment, the complete shell of the shell catalyst is penetrated by the organic binder.

The second embodiment is in particular suitable for shell catalysts comprising a precursor of the catalytically active material that needs a high temperature for activation and in particular needs a temperature for activation that is considerably exceeding the temperature experienced by the catalyst during its designated use in a reactor. Such shell catalysts are commonly not activated in the reactor intended for use of the catalyst but are activated in an activation reactor that is configured for higher temperatures. After activation the activated catalyst is loaded into the reactor for use in the intended reaction.

An exemplary shell catalyst with low attrition resistance is a catalyst based on bismuth/molybdenum for the production of acrolein. This catalyst comprises an inert support body, which is coated with a layer of the catalytically active material forming a shell around the inert support body. For the coating process a suitable organic binder has to be used, in order to ensure that the shell adheres to the inert support body. This coating procedure is well established and is e.g. known from the production of other shell catalysts, such as a catalyst for the production of phthalic anhydride. Usually the organic binder of such shell catalyst is removed in situ during reactor heat up. In the case of the catalyst for the production of acrolein, the catalyst has to be thermally activated at a temperature of about 600° C. which is significantly higher than the reaction temperatures, which is about 330° C. During this high temperature activation the organic binder is removed without any residue. After the removal of the organic binder the shell comprising the catalytically active material shows very poor adhesion to the inert support body. During catalyst handling, e.g. filling in drums, catalyst loading into the reactor, etc. very strong dust formation occurs, due to abrasion. Actually the adhesion of the shell is so poor that during catalyst handling almost the complete shell falls off. This can be prevented by application of a protective coating, comprising an organic binder, e.g. acryl/methacrylate by the method according to the invention.

The catalytically active material, according to an embodiment present in the form of a precursor of the catalytically active material, according to an embodiment is provided in powder form. The particle size of the powder particles is chosen suitable for the method used for shaping the catalyst body. When extrusion or tabletting is used for shaping the catalyst body, a suitable particle size is e.g. a range of 10 to 200 μm. When using spraying for shaping the catalyst body, e.g. for coating an inert support body with a shell of a pre-stage catalyst material to obtain a pre-stage shell catalyst body, a suspension of a finer precursor material can be used having a particle size within a range of e.g. 1 to 150 μm.

However, other particle sizes may be used as well. The particle size can be adjusted by common methods, e.g. by sieving.

Adjuvants, such as for example tabletting aids or pore formers, can also be added to the catalyst material. Tabletting aids are usually catalytically inert and improve the tabletting properties of the catalyst material, for example by increasing the slip and/or flow properties. A particularly suitable tabletting aid is for example graphite. The added tabletting aids can remain in the activated catalyst and are present according to an embodiment in an order of from 1 to 5 wt.-% in the catalyst body relative to the total weight of the catalyst material.

In addition, the catalyst material can contain pore formers. Pore formers are substances that are used for the targeted setting of the pore structure in the meso- and macropore range. As a rule, these are compounds containing carbon, hydrogen, oxygen and/or nitrogen which are added to the catalyst precursor powder before shaping and decompose or evaporate during the subsequent activation of the catalyst body or catalyst mould, for example by calcining.

After shaping the catalyst body is provided at least in parts of its surface with an organic binder which after penetration into the catalyst body provides a protective coating at the surface of the catalyst mould.

Preferably, the whole surface of the catalyst body is provided with an organic binder thereby providing a catalyst mould with a surface formed by the protective coating. The binder, in particular the organic binder, can be applied by any known method.

For example, the application of the organic binder can be carried out in a coating drum or in a fluidized bed coater. According to an embodiment, a dispersion or a solution of the organic binder is sprayed onto agitated catalyst bodies. For this intention, the catalyst bodies can be conveyed along the spray site using e.g. a screening and conveying machine.

As described already further above, suitable organic binders according to an embodiment are polymers which can be removed completely by heating to about 300 to 400° C. Such organic binders are known in the state of the art and are used, for example, for the production of core-shell catalysts. Suitable organic binders are e.g. polyvinyl acetates, starches, modified starches, dextrines, and dextrines being modified with a plasticizer, e.g. poly propylene.

The production of the catalyst moulds is done preferably in that first a forming step is carried out, for example, in a tablet press machine, to obtain catalyst bodies.

Then, according to an embodiment, the catalyst bodies can be calcined (according to an embodiment immediately after pressing) thereby already obtaining a particular stability. This allows easier handling of the catalyst bodies during application of the organic binder.

The organic binder is applied onto the, optionally calcined, catalyst bodies, e.g. by spraying a solution or dispersion of the organic binder onto the catalyst bodies or by impregnating the catalyst bodies with e.g. a solution, an emulsion or a suspension of the organic binder. The organic binder penetrates the surface of the catalyst bodies to thereby form a protective coating on the surface of the catalyst bodies.

In a further step, according to an embodiment, the sprayed-on catalyst bodies can be dried to obtain the stabilized catalyst moulds.

In plant production the protective coating formed by penetration of the binder into an outer layer of the catalyst body, can be applied by the use of a fluidized-bed coater.

According to an embodiment, a drum coater, e.g. a mixer similar to a modified cement mixer, is used for applying the organic binder to the catalyst body surface. Here a dispersion or solution of the binder, e.g. polyvinyl acetate, in a suitable solvent, e.g. water, is sprayed onto the catalyst bodies, while the catalyst bodies are carefully mixed and agitated in the cement mixer. After the application of the protective coating the catalyst moulds can be dried by e.g. using an air blower, while agitating of the catalyst moulds in the cement mixer is continued.

According to a further embodiment of the method of the invention, the application of the protective coating is performed by use of a screening and conveying machine. This machine basically comprises a box with a sieve bottom. The box is set into vibration by connected unbalanced motors. If catalyst bodies are applied to one end of the box, the catalyst bodies will move by "jumping" on the sieve bottom from one end of the box to the other, from where the catalyst moulds can exit e.g. into a drum. While the individual catalyst bodies are moving across the box on the sieve bottom, fines and fragments are removed. At the same time the protective coating is applied to the catalyst bodies. This happens e.g. by use of spray nozzles that are installed above the box. After the spraying section the catalyst moulds can be dried by use of e.g. an air blower or by the use of UV drying lamps that also are installed above the box, before the catalyst moulds exit the box by falling e.g. into a catalyst drum.

According to an embodiment, a solution and/or dispersion of the organic binder in at least one solvent is provided and the solution and/or dispersion of the organic binder is applied to the surface of the catalyst body.

For preparation of the solution or the dispersion a suitable solvent is selected. The solvent should have a low boiling point such that the solvent can be evaporated easily after application of the solution or dispersion to the catalyst body. Suitable solvents are e.g. alcohols, like methanol, ethanol or propanol. A preferred solvent is water.

The amount of organic binder dispersed or dissolved in the solvent is suitably selected according to the type of organic binder used and according to the method used for applying the binder solution or dispersion to the catalyst bodies.

According to an embodiment the amount of organic binder comprised in the solution or dispersion of the organic binder is selected within a range of 5 to 20 wt. %.

In an embodiment, the solution and/or dispersion of the organic binder is applied onto surface of the catalyst body by spraying. Preferably, the spraying occurs under agitation of the catalyst moulds. In a preferred embodiment, the spraying of the solution and/or dispersion of the organic binder onto surface of the catalyst body occurs at an elevated temperature and under aeration. A suitable temperature range is according to an embodiment a range of 20 to 60° C. However, depending on the solvent used, also higher temperatures above 60° C. may be used.

The speed of application of the solution or dispersion of the organic binder is selected such that according to an embodiment the catalyst bodies are not wetted but the solvent is adsorbed quickly by the catalyst bodies.

In a further embodiment, after the organic binder has been applied, the catalyst moulds are dried at an elevated temperature to remove the at least one solvent of the solution and/or dispersion. A suitable temperature range is according to an embodiment a range of 20 to 80° C. The drying can be carried out according to an embodiment by an air blower or UV-drying lamps.

After drying, the catalyst moulds are free-flowing.

The catalyst moulds obtained by the method according to the invention therefore can easily be filled into a reactor, e.g. the tubes of a reactor, without experiencing considerable dust formation.

After filling of the reactor, the organic binder can easily be removed.

For removal of the organic binder, the catalyst moulds can be calcined at elevated temperature, according to an embodiment at a temperature of at least 200° C., according to a further embodiment of at least 300° C. According to a further embodiment, the calcinations of the catalyst moulds is performed at a temperature of less than 400° C.

According to an embodiment, calcination is performed in the presence of air or nitrogen. The duration of the calcination is depending on the amount of catalyst mould treated and can be determined by e.g. analyzing the gas at the exit of a reactor.

In a preferred manner, calcination is carried out after the catalyst moulds have been filled into a reactor, in which then the proper reaction is to be carried out. In other words, the catalyst moulds are filled into the reactor in a condition where the protective coating is present and after calcination and removal of the protective coating, the proper reaction catalysed by the catalyst can be started.

The method of the present invention is neither limited to a particular catalyst nor to a particular reaction catalyzed by this catalyst, such as the catalyst for the production of maleic anhydride or formaldehyde. These examples are merely mentioned to demonstrate the general applicability of the present invention to all catalysts, whose production and use is accompanied with dust formation, which should be minimized.

Moreover, the method of the present invention can be applied to catalysts independently of their geometry or shape. It may be the case that a particular geometry of a catalyst tends more to dust formation than another one. Nevertheless the formation of dust and the geometry of catalysts are generally two independent parameters.

The claimed invention will be explained in more detail by way of examples and with reference to the accompanying figures, wherein:

In order to demonstrate the suitability of a copolymer of vinyl acetate and ethylene, acrylic/methacrylate, and hydroxyethyl cellulose for formation of a protective coating to obtain dust free stabilized catalyst moulds, laboratory samples were made as described below. These samples, plus a sample of an untreated catalyst body were used to carry out the following tests:
 a) Abrasion & attrition test on a sieve machine
 b) Dust formation test
 c) Thermo-gravimetrical analysis Test Methods:
a) Abrasion & Attrition Test on a Sieve Machine To simulate catalyst dust formation caused by abrasion and attrition during catalyst handling, catalyst samples were treated on a sieve machine. An amount of 500 g catalyst samples (untreated catalyst bodies and catalyst moulds comprising a protective coating according to the present invention) were placed on the sieve machine. The weight of the fraction passed through the sieve was weighted (in g).

Test parameter:
 Sieve Machine: Retsch AS 200
 Amplitude: 100
 Mesh opening of sieve: 500 μm
 Test duration: 10 minutes b) Dust Measurement To simulate catalyst dust formation in ambient atmosphere during reactor loading, a dust measurement was carried out. In order to quantify the dust development, catalyst samples were poured into a 10 liter bucket. Then the dust formation was measured at about 10 cm above the bucket for a period of 10 minutes.

Test parameter:
 Dust Measurement Device: Dust Trak II Modell 8530, Driesen & Kern GmbH;
 Amount of catalyst: 1000 ml
 Falling Height: 75 cm c) Thermo-Gravimetrical Analysis In order to simulate the "burn-off behaviour" of the protective coating during the start-up of the reactor, two thermo-gravimetrical analyses were carried out. For the first analysis air was used as carrier gas, and for the second analysis nitrogen was used as carrier gas.

Test Parameter:
 Device: Netzsch STA 409 PG
 Carrier gas: air & nitrogen
 1. Heating rate: 2° C. per minute
 Start temperature: 20° C.
 1. End temperature: 200° C.
 Holding time at 200° C.: 3 hours
 2. Heating rate: 2° C. per minute
 2. End temperature: 400° C.

Figure 3:
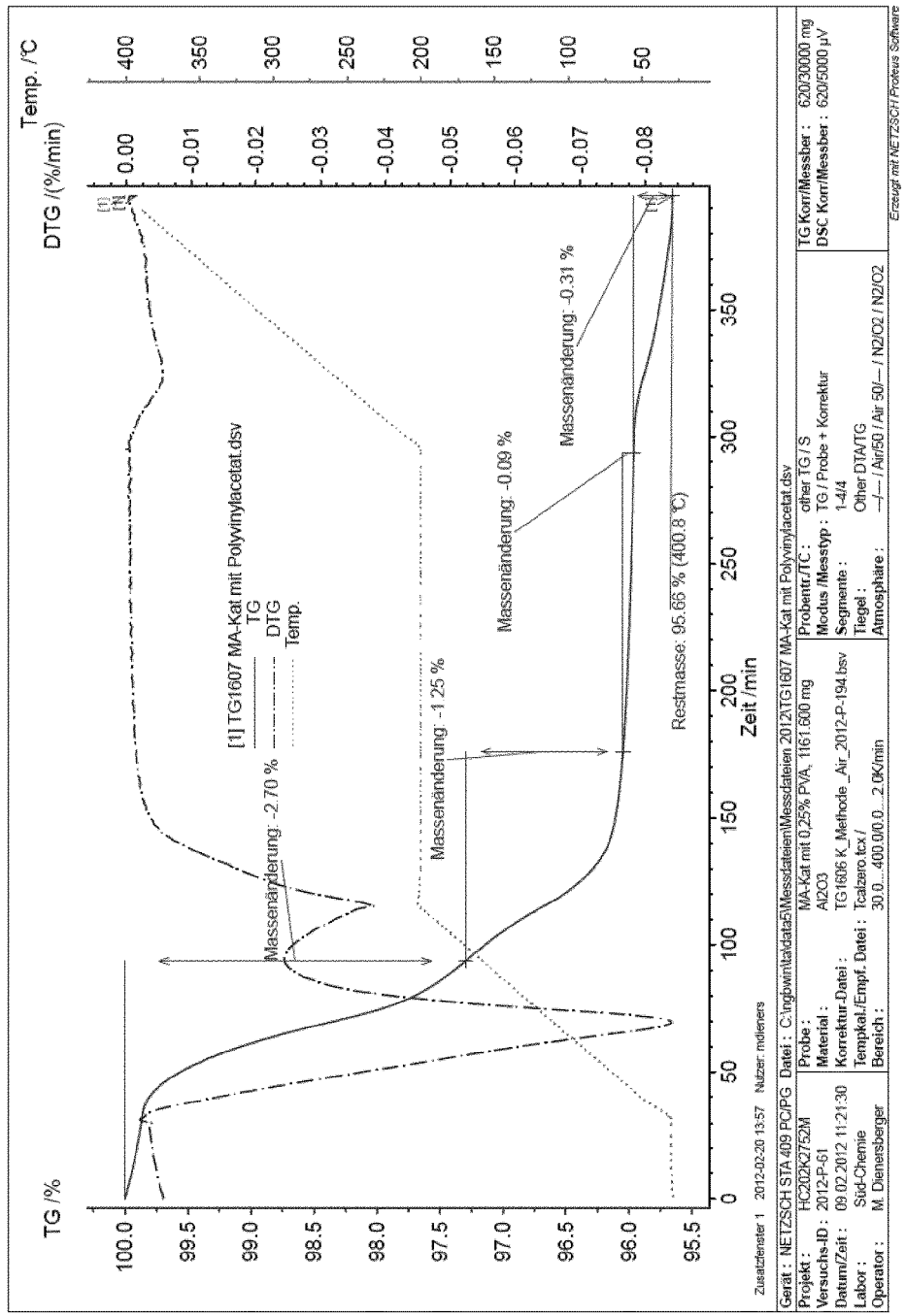
FIG. 3 shows a diagram of a thermo-gravimetric analysis of a VPO-catalyst according to the invention (sample B) wherein air is used as carrier gas.
Figure 4:
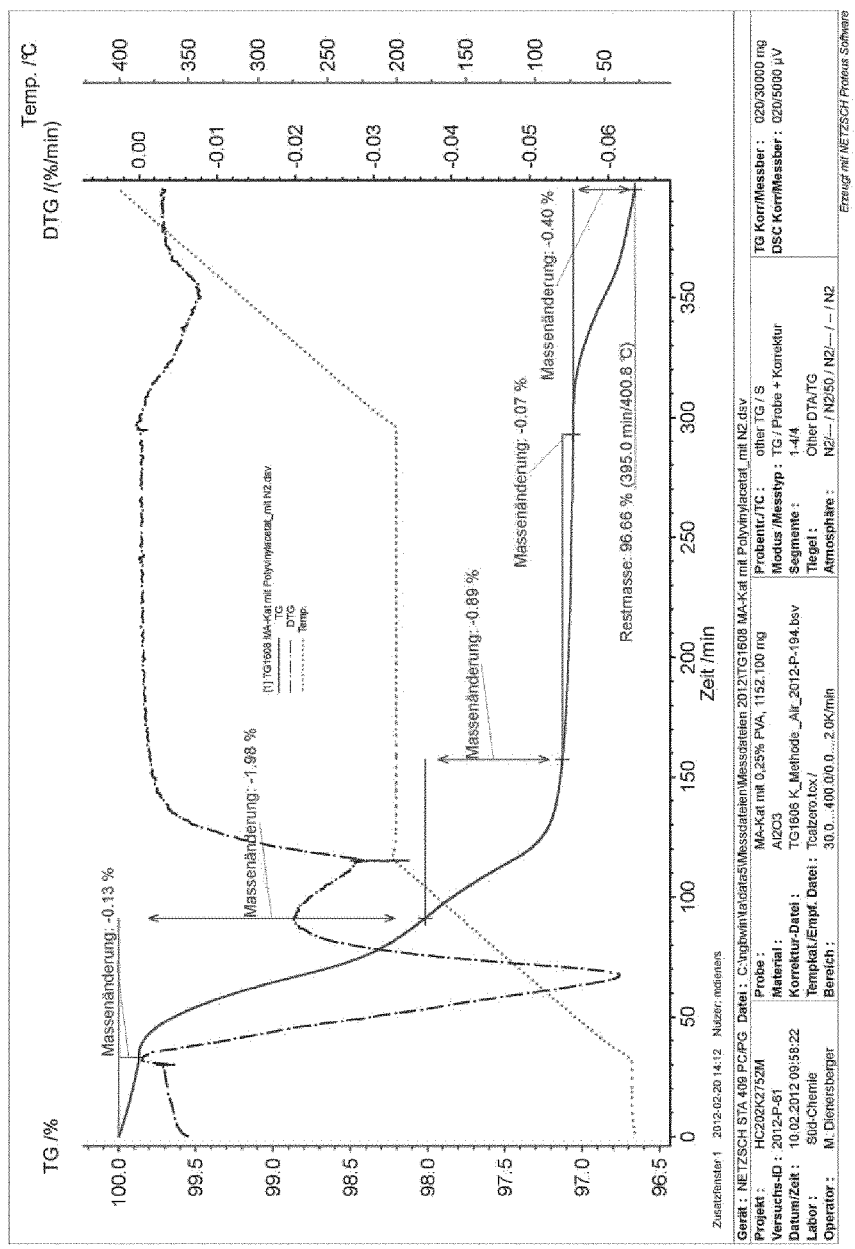
FIG. 4 shows a diagram of a thermo-gravimetric analysis of a VPO-catalyst without a protective coating (sample F), wherein nitrogen is used as carrier gas.

The test results are shown in FIGS. 3 and 4.

d) Performance Tests

For the performance test a bench scale reactor was used comprising four 21 mm I.D. reaction tubes, which were placed in a heated and stirred salt bath.

Each tube was filled with 68 grams of a VPO-catalyst sample diluted with 272 inert rings. Some of the tubes were filled with VPO-catalyst provided with a protective coating according to the invention obtained by application of 0.5 weight-% of a copolymer of vinyl acetate and ethylene. Some tubes were filled with uncoated VPO-catalyst. The filling height of all tubes was 100 cm.

Figure 5:
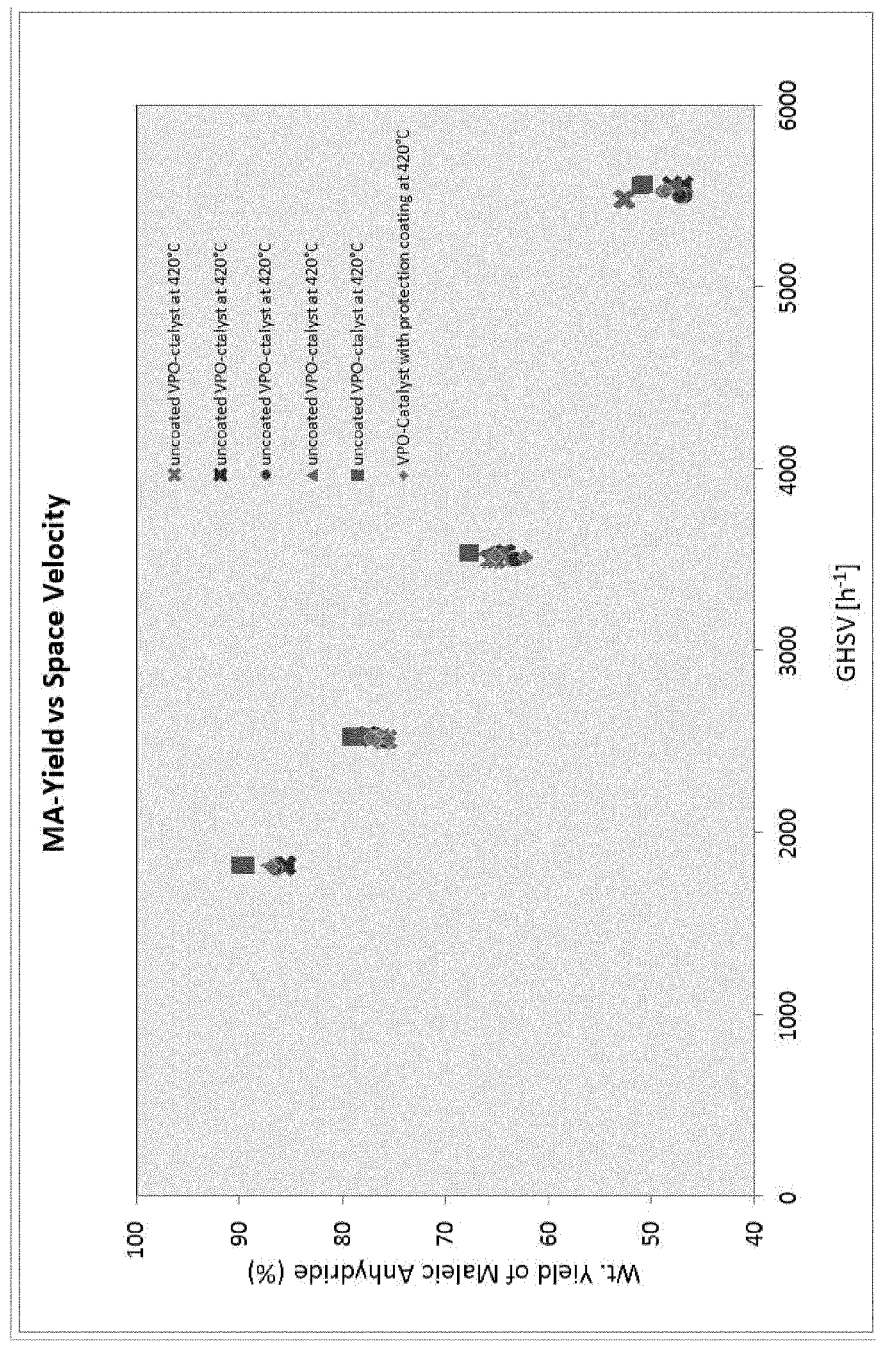
FIG. 5 shows a diagram wherein the maleic anhydride yield is assigned versus the space velocity of the reaction gas for various catalyst samples.
Figure 6:
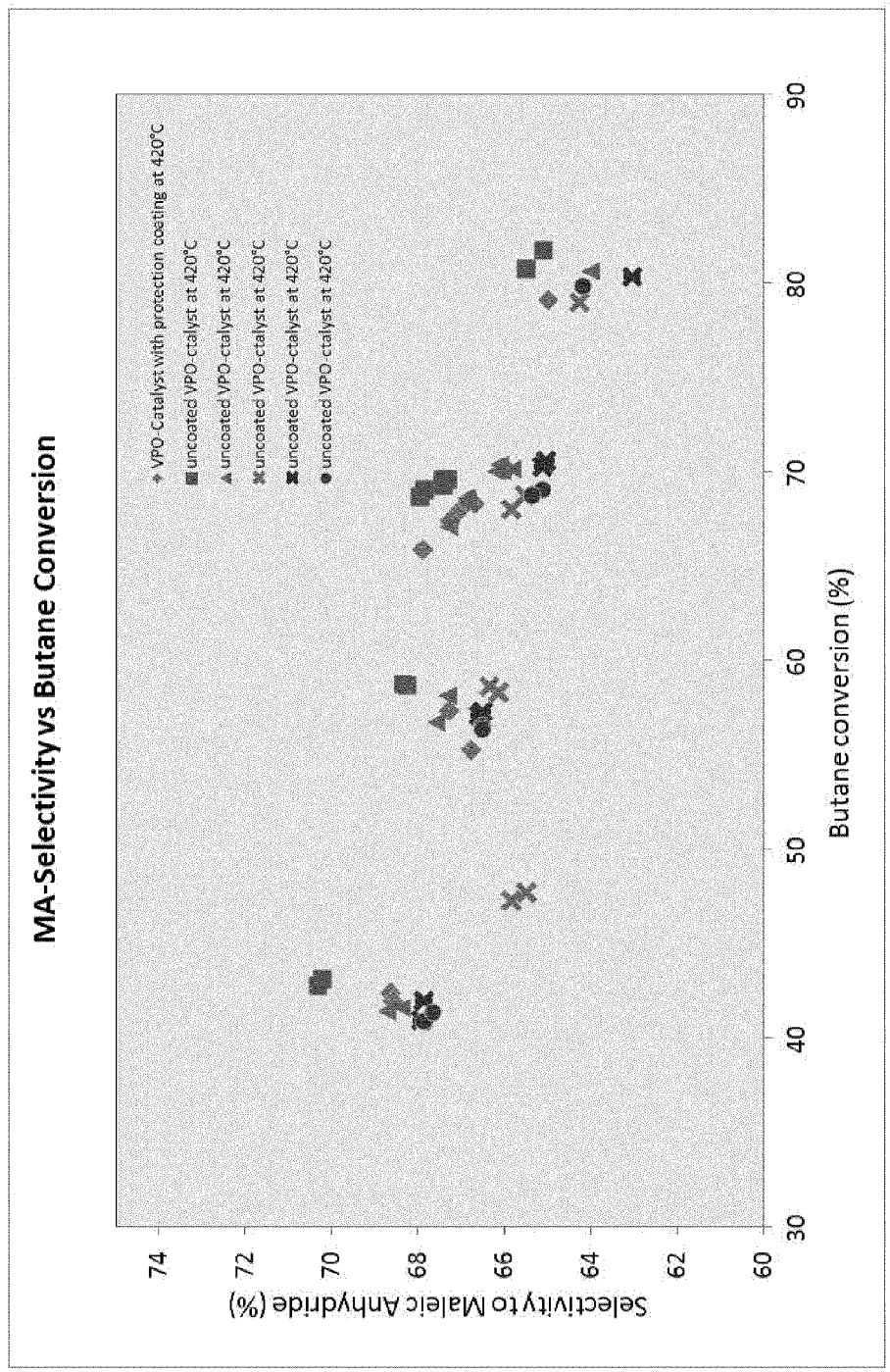
FIG. 6 shows a diagram wherein the maleic anhydride selectivity is displayed versus the butane conversion rate.

The reactor was heated up to 360° C. under an air flow of 425 SCM/hour (SCM: standard cubic meter; gas volume at 1.01325 hPa, 0% humidity, 273.15 K). Then butane feed was introduced. The concentration of butane in the feed flow was 1.5 vol. % and the concentration of air in the feed flow was 98.5 vol. %. The reactor was further heated up to 420° C. and was left under these conditions for 72 hour for equilibration. The catalyst performance (MA yield and MA selectivity) was measured at space velocities [liter gas per liter catalyst per hour] of 1800 $h^{-1}$, 2500 $h^{-1}$, 3500 $h^{-1}$ and 5500 $h^{-1}$. MA yield, MA conversion and MA selectivity, as given in FIGS. 5 & 6, were calculated from butane inlet concentration, butane outlet concentration, CO outlet concentration, $CO_2$ outlet concentration and MA outlet concentration, which were measured by an IR-Analyzer and a gas chromatograph (MA: maleic anhydride).

Laboratory Experiments:
1. Manufacturing of a Protective Coating with 0.1 Weight-% of a Copolymer of Vinyl Acetate and Ethylene (Sample A)
 1000 g of VPO-catalyst were dried at 120° C. for 16 hours.
 2 grams of a dispersion of a copolymer of vinyl acetate and ethylene (50% solid content) were dispersed in 20 grams of demineralised water.
 This dispersion was filled into a spray gun, as commonly used for painting.
 The dried catalyst rings were filled in a 10 liter drum.
 The copolymer dispersion was sprayed as a fine mist onto the catalyst rings. During this procedure, the catalyst was permanently moved by carefully shaking the 10 liter drum in order to ensure a homogeneous coating.
 Finally, the coating was dried under hot air.
2. Manufacturing of a Protective Coating with 0.25 Weight-% of Polyvinyl Acetate (Sample B)
 1000 g of the same VPO-catalyst used in experiment 1 were dried at 120° C. for 16 hours.
 5 grams of the same polyvinyl acetate dispersion (50% solid content) used in experiment 1 were dispersed in 20 grams of demineralised water.
 This dispersion was filled into a spray gun, as used for painting.
 The dried catalyst bodies were filled in a 10 liter drum.
 The polyvinyl acetate dispersion was sprayed as a fine mist onto the catalyst rings. During this procedure, the catalyst bodies were permanently agitated by carefully shaking the 10 liter drum in order to ensure homogeneous coating.
 Finally, the catalyst moulds were dried under hot air.
3. Manufacturing of a Protective Coating with 0.5 Weight-% of a Copolymer of Vinyl Acetate and Ethylene (Sample C)
 Manufacturing example 2 was repeated with an increased amount of polyvinyl acetate polymer to obtain a catalyst mould with 0.5 wt. % polymer (sample C)
4. Manufacturing of a Protective Coating with 0.50 Weight-% of Acrylic/Methacrylate (Sample D)
 1000 g of VPO-catalyst were dried at 120° C. for 16 hours.
 11.9 grams of commercially available acrylic/methacrylate dispersion (42% solid content) was dispersed in 15 grams of demineralised water.

This dispersion was filled into a spray gun, as used for painting.

The dried catalyst bodies were filled in a 10 liter drum.

The polyvinyl acetate dispersion was sprayed as a fine mist onto the catalyst rings. During this procedure, the catalyst bodies were permanently agitated by carefully shaking the 10 liter drum in order to ensure a homogeneous coating.

Finally, the catalyst moulds were dried under hot air.

5. Manufacturing of Protective a Coating with 0.05 Weight-% of Hydroxyethyl Cellulose (Sample E)

1000 g of commercial MA catalyst were dried at 120° C. for 16 hours.

1 gram of hydroxyethyl cellulose was dispersed in 40 g demineralized water by stirring. Stirring was continued for 2 hours until the hydroxyethyl cellulose completely dissolved and developed a stable viscosity.

This solution was filled into a spray gun, as it is used for painting.

The dried catalyst bodies were filled in a 10 liter drum.

The hydroxyethyl cellulose solution was sprayed as a fine mist onto the catalyst rings. During this procedure the catalyst bodies were permanently agitated by carefully shaking the 10 liter drum in order to ensure homogeneous coating.

Finally, the coating was dried under hot air.

An untreated sample of the VPO-catalyst was tested as sample F.

Samples A to F were tested to their attrition and abrasion behaviour according to the test described above. Test F was repeated as a control (sample F'). The amount of catalyst material abraded during the test for each sample is summarized in table 1 and displayed in FIG. 1.

TABLE 1 amount of catalyst material abraded during Abrasion & Attrition Test on a Sieve Machine

| | Sample | | | | | | |
|---|---|---|---|---|---|---|---|
| | A | B | C | D | E | F | F' |
| Amount (g/500 g) | 0.0988 | 0.052 | 0.0331 | 0.05 | 0.3445 | 0.3728 | 0.24 |

Figure 1:
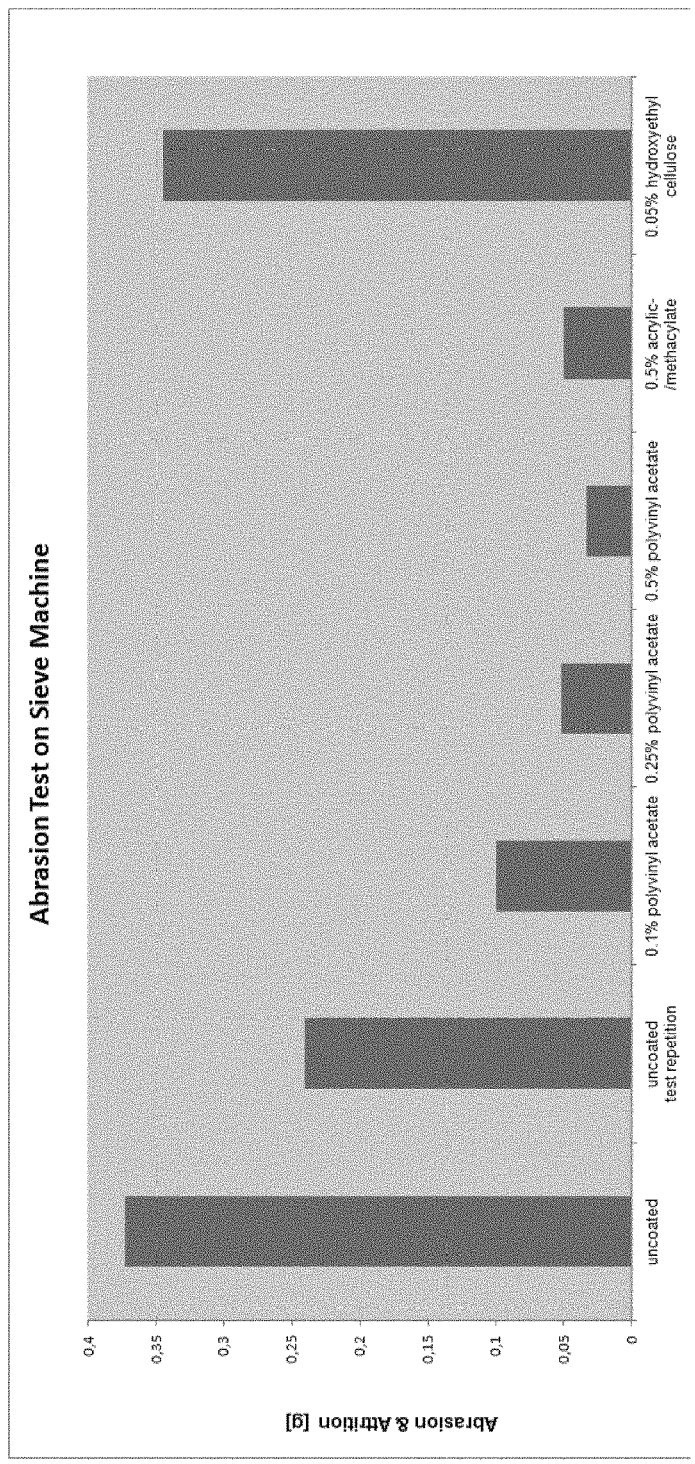
FIG. 1 shows in comparison the amount of abraded catalyst material experienced by a vanadium phosphorous oxide catalyst (VPO-catalyst) in an abrasion and attrition test on a sieve and conveying machine according to test method a)

The results of the abrasion & attrition test are displayed in FIG. 1.

FIG. 1 shows that by applying 0.1, 0.25, and 0.5 weight-% of polyvinyl acetate or 0.5 wt. % of acrylic/methacrylate (samples A to D) a considerable reduction in dust development can be achieved. It further demonstrates that application of 0.05 weight-% of hydroxyethyl cellulose (sample E) results only in a minor reduction of abrasion and attrition compared with the untreated catalyst mould (sample F, F').

Figure 2:
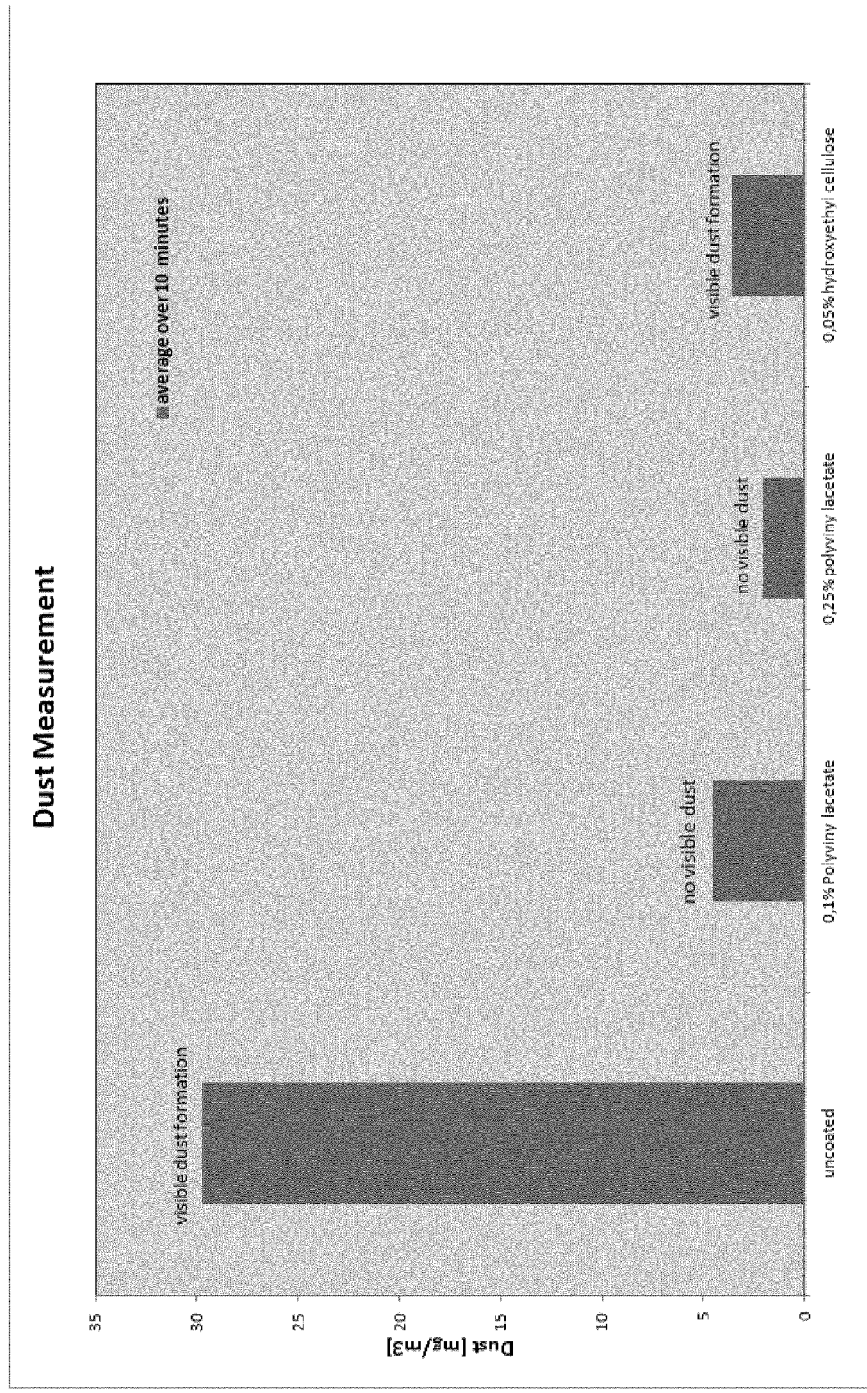
FIG. 2 shows the amount of dust in air developed during a dust measurement test according to test method b)

The results of the dust measurement tests are summarized in table 2 and are shown in FIG. 2.

TABLE 2 amount of dust measured in dust measurement test

| | Sample | | | |
|---|---|---|---|---|
| | A | B | E | F |
| Amount mg/m$^3$ | 4.5 | 2.1 | 3.6 | 29.7 |

The visible dust formation (in mg dust per m$^3$ air) was measured to compare the uncoated catalyst moulds (sample F) and those treated with 0.1 and 0.25 weight-% of polyvinyl acetate (samples A, B), each in relation to the weight of the catalyst mould, as well as 0.05 weight-% of hydroxyethyl cellulose (sample E) with respect to the weight of the catalyst mould. Whereas no visible dust formation has been observed for samples A, B, the dust formation for untreated catalyst moulds (sample F) and for those treated with 0.05 weight-% hydroxyethyl cellulose (sample E) was visible.

The results of the tests show, that the abrasion and attrition as well as dust formation during catalyst handling can be minimized by the application of a protective coating with 0.1 weight-% to 0.5 weight-% of a copolymer of vinyl acetate and ethylene or by the application 0.5 weight-% to 1.0 weight-% of acylic/methacrylate.

The protective coating of 0.1 weight-% of a copolymer of vinyl acetate and ethylene leads to a reduction of fines by 73.5% after the abrasion and attrition test (see FIG. 1). The protective coating of 0.25 weight-% of a copolymer of vinyl acetate and ethylene leads to a reduction of fines by 86.1% after the abrasion and attrition test and the protective coating of 0.50 weight-% polymer leads to the reduction of fines by even 91.1%. The protective coating of 0.5 weight-% acrylic/methacrylate leads to a reduction of fines by 86.6%.

It has to be considered that the mechanical stress to the catalyst rings during this abrasion and attrition test is significantly higher than during usual catalyst handling for reactor loading. Therefore, the reduction of catalyst dust formation during reactor loading is much higher as the test shows.

The protective coating of 0.1 weight-% of a copolymer of vinyl acetate and ethylene leads to a reduction of fines in the ambient air by 84.8% according to the dust formation test. The protective coating of 0.25 weight-% of a copolymer of vinyl acetate and ethylene leads to a reduction of fines by even 92.9% after dust formation test (see FIG. 2). Also this test is much rougher than catalyst handling in real life. Therefore the reduction of catalyst dust formation during reactor loading is much higher as the test shows.

The thermo-gravimetrical analyses of sample B show that the protective coating had been completely burnt-off after a temperature of 400° C. had been reached, regardless whether air or nitrogen was used as a carrier gas (see FIGS. 3 and 4).

The reaction conditions and results of the performance tests performed with samples B and F are summarized in tables 3 to 6. The results of the performance tests are also graphically displayed in FIGS. 5 and 6.

TABLE 3 maleic anhydride yield and residence time determined during performance test on sample B

| Time | (h:min) | 0 | 3:19 | 7:58 | 12:18 | 16:37 | 32:04 | 35:42 | 40:14 | 45:14 | 49:26 |
|---|---|---|---|---|---|---|---|---|---|---|---|
| GHSV, m | l/kg/h | 5557.26 | 5554.63 | 3534.92 | 3536.99 | 1815.30 | 1815.64 | 2523.04 | 2525.25 | 2522.57 | 2522.41 |
| t, mod | g * s/ml | 0.274 | 0.274 | 0.421 | 0.420 | 0.809 | 0.584 | 0.584 | 0.583 | 0.586 | 0.581 |
| Conv. | % | 42.36 | 41.95 | 55.20 | 57.28 | 79.09 | 67.87 | 67.36 | 68.26 | 65.82 | 68.37 |
| Yield | wt-% | 49.15 | 48.63 | 62.30 | 65.15 | 86.89 | 76.95 | 76.57 | 76.95 | 75.53 | 77.25 |
| Select. | mol-% | 68.66 | 68.61 | 66.79 | 67.31 | 65.01 | 67.09 | 67.26 | 66.71 | 67.91 | 66.87 |

TABLE 4 maleic anhydride yield and residence time determined during performance test on sample F

| Time | (h:min) | 0 | 5:48 | 13:05 | 20:03 | 28:00 | 35:48 | 43:35 | 50:33 | 58:20 | 65:28 |
|---|---|---|---|---|---|---|---|---|---|---|---|
| GHSV, m | l/kg/h | 5557.26 | 5554.63 | 3534.92 | 3536.99 | 1815.30 | 1815.64 | 2523.04 | 2525.25 | 2522.57 | 2522.41 |
| t, mod | g * s/ml | 0.275 | 0.274 | 0.421 | 0.421 | 0.811 | 0.809 | 0.587 | 0.586 | 0.585 | 0.585 |
| Conv. | % | 42.72 | 43.07 | 58.72 | 58.66 | 80.73 | 81.70 | 69.00 | 68.67 | 69.59 | 69.53 |
| Yield | wt-% | 50.77 | 51.11 | 67.84 | 67.65 | 89.37 | 89.91 | 79.12 | 78.85 | 79.16 | 79.22 |
| Select. | mol-% | 70.33 | 70.22 | 68.38 | 68.25 | 65.52 | 65.12 | 67.86 | 67.95 | 67.32 | 67.42 |

The performance test in the pilot plant shows that the removable protective coating does not affect the catalyst performance at all. As is immediately visible form FIGS. 5 and 6 the catalyst comprising a protective coating according to the invention achieves the same yield and selectivity as a catalyst without a protective coating.

These results also show that polyvinyl acetate as a protective coating can be used for all kinds of catalysts, which are heated up to temperatures of at least 400° C. during reactor start-up. It is not relevant, whether this heat-up is carried out under air or nitrogen atmosphere.

Pressure Drop Test
Test Description

A sample of ring shape MA catalyst was filled manually into a 21 mm reactor tube to a total filling height of 390 cm. After every 100 cm the filled catalyst weight and the pressure drop at an air flow of 3.0 Nm³/h was measured. Because the reactor tube had a total length of 400 cm, the last filled increment was just 90 cm. After the reactor tube had been filled with catalyst to a filling height of 390 cm and the pressure drop had been measured, the tube was emptied carefully and the catalyst was collected in a plastic beaker. The unloaded catalyst then was transferred into a 2.5 mm sieve. This sieve was put for 30 seconds on a sieving machine, in order to separate the breakage & fines, which were formed during catalyst loading and unloading, from the catalyst rings. Finally the weight of the breakage & fines was determined on a scale. From the measured catalyst weights for every 100 cm filling height the catalyst filling density for every 100 cm of filled catalyst was calculated.

A second sample of the same ring-shaped MA catalysts was coated with 0.5 wt. % of polyvinyl acetate. After the aqueous coating dispersion had been applied to the catalyst, the sample was dried with a hot air fan, in order to remove all the water. This sample then was used to carry out the same test as described above.

Test Results
Pressure Drop Test

Figure 7:
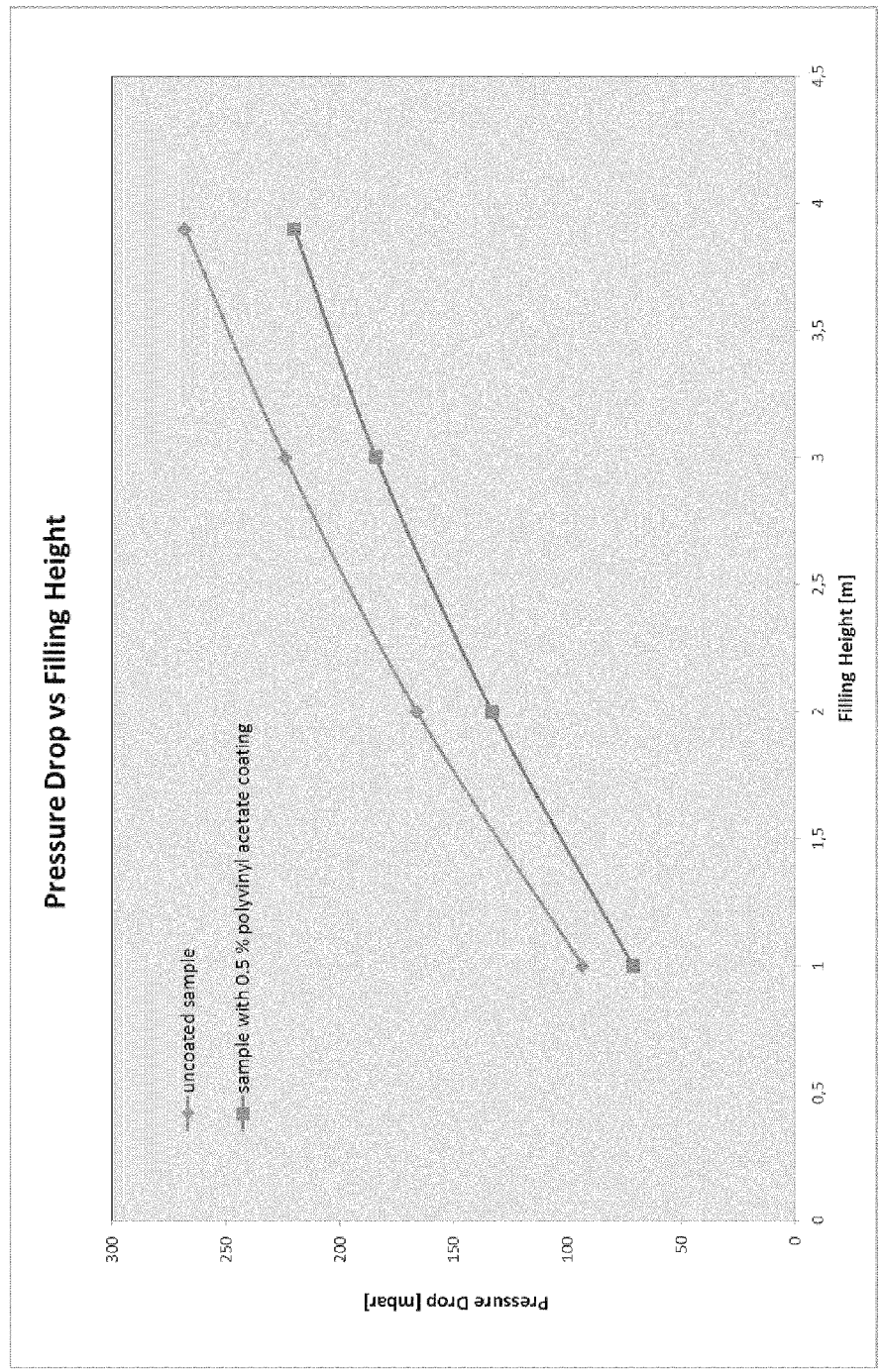
FIG. 7 shows a diagram wherein the pressure drop is displayed versus the filling height of a reactor tube for an uncoated catalyst sample and a catalyst sample according to the invention.

The results of the pressure drop test are summarized in tables 5 and 6 and displayed in FIG. 7.

TABLE 6 pressure drop for uncoated catalyst sample F

| filling height [m] | catalyst mass [g] | Density [g/ml] | delta p at 3 Nm³/h |
|---|---|---|---|
| 1 | 238.8 | 0.689 | 93 |
| 2 | 218.7 | 0.631 | 166 |
| 3 | 213.7 | 0.617 | 224 |
| 3.9 | 185.7 | 0.596 | 268 |

TABLE 7 pressure drop for coated catalyst sample B

| filling height [m] | catalyst mass [g] | density [g/ml] | delta p at 3 Nm³/h |
|---|---|---|---|
| 1 | 215.2 | 0.621 | 71 |
| 2 | 215.8 | 0.623 | 133 |
| 3 | 214.3 | 0.619 | 184 |
| 3.9 | 188.3 | 0.604 | 220 |

In comparison with the uncoated catalyst sample (sample B), the catalyst sample with 0.5% of a protective coating, formed of polyvinyl acetate, showed significant lower pressure drops (see FIG. 7). At a filling height of 390 cm a pressure drop of 268 mbar was measured for the uncoated catalyst sample, whereas the pressure drop for the coated sample was 220 mbar.

Filling Densities

Figure 8:
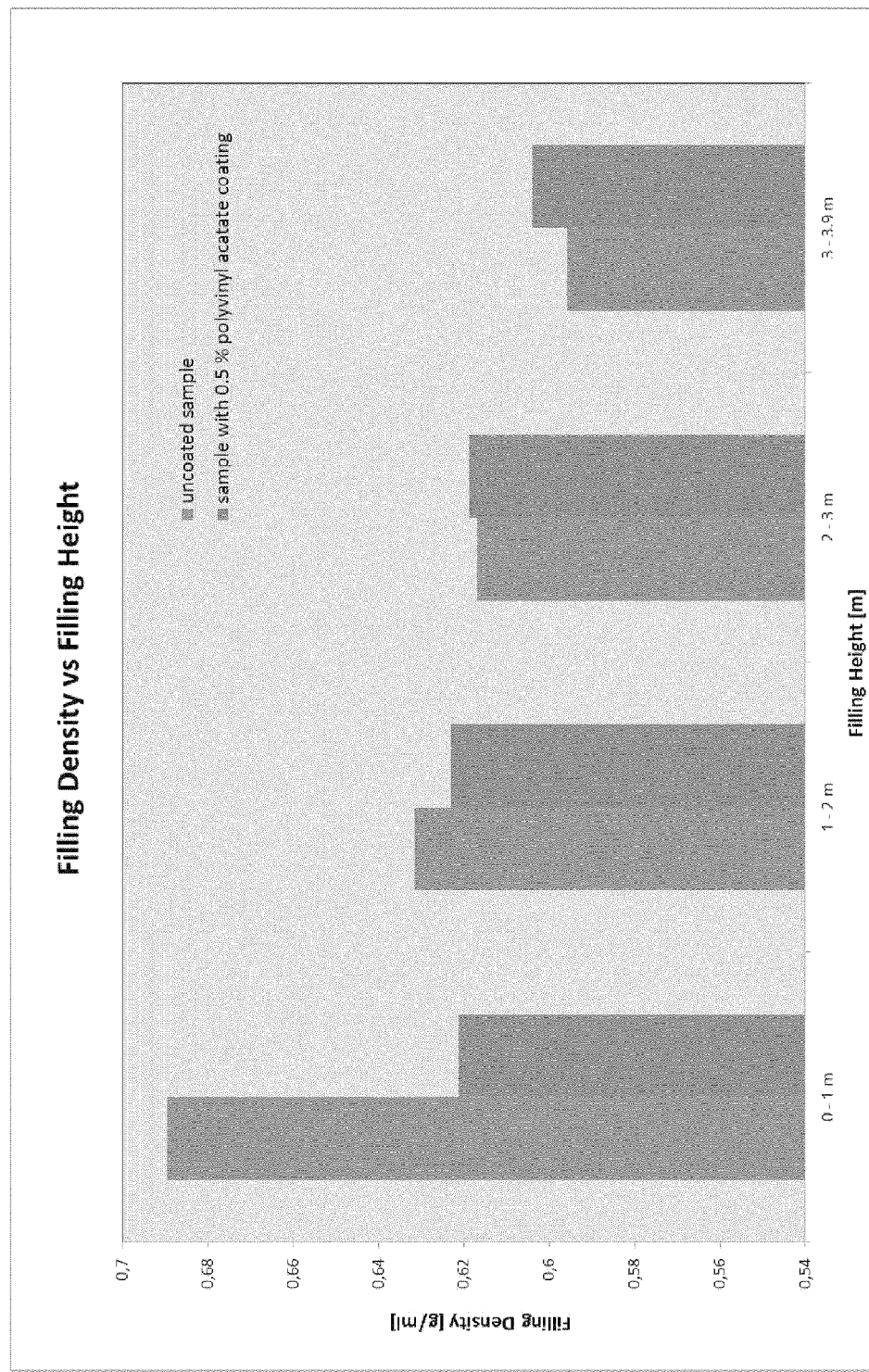
FIG. 8 shows a diagram wherein the filling density of a catalyst package in a reactor tube is recorded for various filling heights of the catalyst.

Data for filling densities depending on filling height are summarized in table 8 and displayed in FIG. 8.

TABLE 8

| filling density and filling height | | | | |
|---|---|---|---|---|
| | Filling height (m) | | | |
| | 0-1 | 1-2 | 2-3 | 3-3.9 |
| Density sample F (g/ml) | 0.689 | 0.631 | 0.617 | 0.595 |
| Density sample B (g/ml) | 0.621 | 0.623 | 0.618 | 0.604 |

The filling densities, which were determined for every 100 cm, showed a significant gradient for the uncoated catalyst sample, whereas the filling densities for the sample with the protective coating showed almost no gradient (see FIG. 8).

Formation of Breakage and Fines

Figure 9:
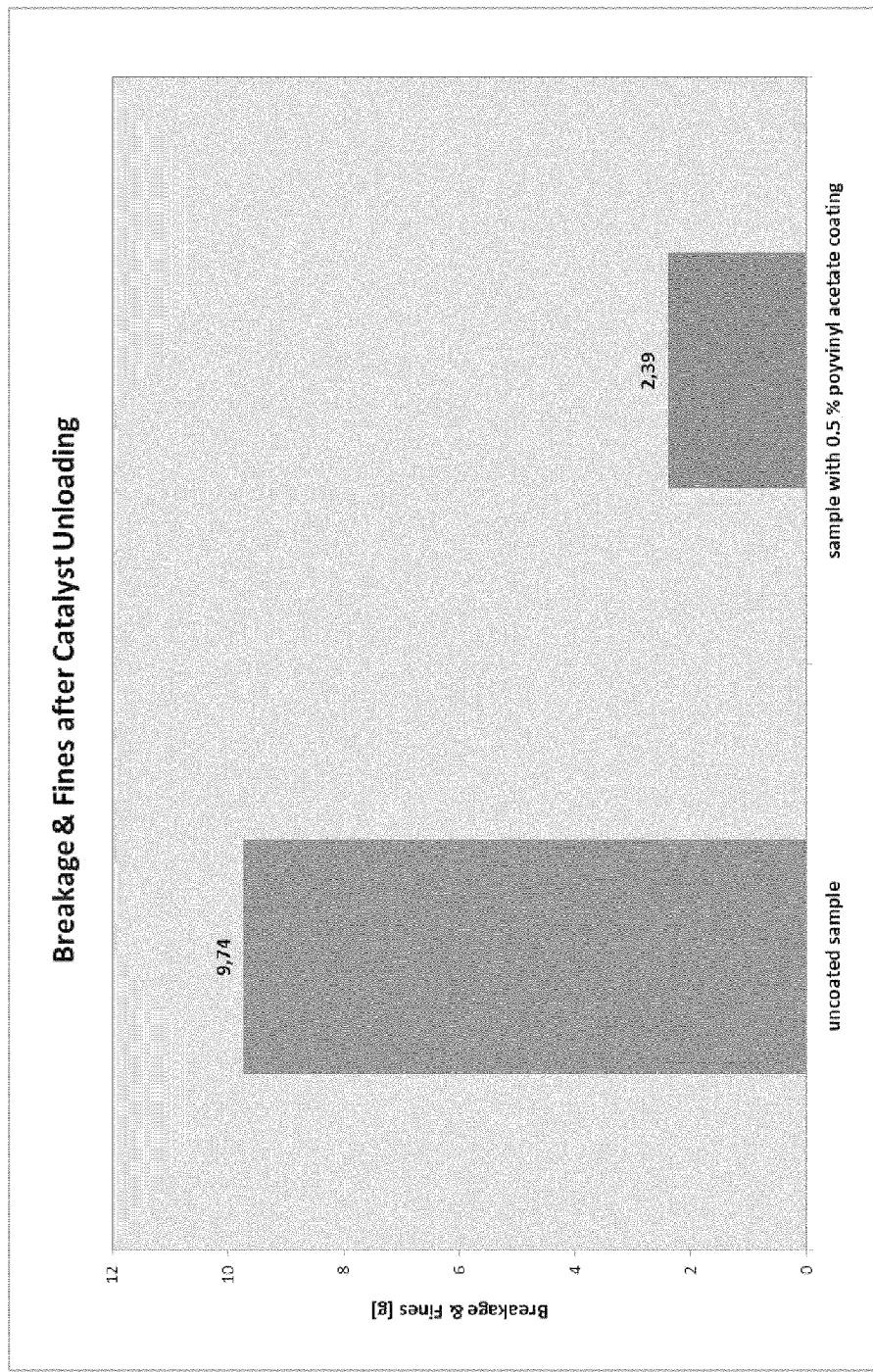
FIG. 9 shows a diagram wherein the amount of breakage and fines obtained by catalyst filling into a reactor tube is displayed for an uncoated catalyst sample and a catalyst sample according to the invention.

The amount of fines determined for samples B and F are summarized in table 9 and displayed in FIG. 9.

TABLE 9

| amount of breakage and fines | |
|---|---|
| Sample | Amount of fines (g) |
| F | 9.74 |
| B | 2.39 |

Also the formation of breakage & fines was about four times higher for the uncoated catalyst sample in comparison with the coated sample (see FIG. 9).

It is assumed that a lot of breakage occurs during reactor tube loading. This significant breakage & fines formation leads to a more dense packing of the catalyst moulds, which finally results in higher pressure drops. The gradient of the filling densities shows that the deeper the catalyst moulds fall down the tube, the more breakage occurs. It has to be considered that for this test a reactor tube was only filled to a filling height of 390 cm, whereas a typical filling height for an industrial scale reactor is 550 cm. Therefore it has to be assumed that even more breakage and fines formation will occur during the filling of an industrial scale reactor.

These results clearly show that the application of a protective coating significantly reduces the formation of breakage & fines during reactor tube loading, resulting in significant lower pressure drops and more uniform filling density of the tube length. Therefore the application of a protective coating does not just prevent hazardous dust formation for the environment and for health, but also can give a technical benefit, if it is considered that the pressure drop over the reactor directly relates to the electrical energy consumption of the compressor.

The invention claimed is:

1. A stabilized catalyst mould comprising a catalyst body formed of a catalyst material, said catalyst material comprising a catalytically active material or a precursor material of the catalytically active material, with a catalytically active material having a composition according to the general formula $$VP_xO_yM_z$$

wherein M is a promoter selected from the group formed of chromium, nickel, magnesium, aluminum, silicon, wolfram, niobium, antimony, caesium, and their mixtures, x is a number between 0.1 and 3, y is a number according to the valence of V, P and M, and z is a number between 0 and 1.5, characterized in that at least parts of the surface of the catalyst mould are provided with a protective coating consisting of an organic binder, characterized in that the amount of the organic binder comprised in the catalyst mould is at least 0.05 weight-% and at most 1.0 weight-%, and the thickness of the protective coating is at most 300 µm, wherein the organic binder comprises a copolymer of vinyl acetate and a further monomer.

2. The catalyst mould according to claim 1, wherein the further monomer is ethylene, propylene, maleic anhydride or a combination thereof.

3. The catalyst mould according to claim 1, wherein the organic binder has an average molecular weight of at least 100 g/mol.

4. The catalyst mould according to claim 1, wherein the catalyst body is formed in its entirety of catalyst material or formed of an inert support core surrounded by at least one layer of catalyst material.

5. The catalyst mould according to claim 1, wherein the catalyst has a maximum extension of 20 mm.

* * * * *